(12) United States Patent
Park et al.

(10) Patent No.: US 10,651,391 B2
(45) Date of Patent: *May 12, 2020

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si, Chungcheongnam-do (KR)

(72) Inventors: Jong Gwang Park, Ulsan (KR); Yun Suk Lee, Seongnam-si (KR); Ki Ho So, Cheonan-si (KR); Hyoung Keun Park, Chuncheon-si (KR); Yeon Seok Jeong, Gangwon-do (KR); Jung Hwan Park, Hwaseong-si (KR); Sun Hee Lee, Hwaseong-si (KR); Gyu Min Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/384,310

(22) Filed: Apr. 15, 2019

(65) Prior Publication Data

US 2019/0245148 A1 Aug. 8, 2019

Related U.S. Application Data

(63) Continuation of application No. 15/427,363, filed on Feb. 8, 2017, now Pat. No. 10,319,915.

(30) Foreign Application Priority Data

Feb. 11, 2016 (KR) .................. 10-2016-0015595

(51) Int. Cl.
*H01L 51/50* (2006.01)
*H01L 51/00* (2006.01)
(Continued)

(52) U.S. Cl.
CPC ........ *H01L 51/0061* (2013.01); *C07D 333/76* (2013.01); *C07D 409/12* (2013.01); *C07D 409/14* (2013.01); *C09K 11/06* (2013.01); *H01L 51/0074* (2013.01); *H05B 33/14* (2013.01); *C09K 2211/1007* (2013.01); *C09K 2211/1014* (2013.01); *C09K 2211/1029* (2013.01); *C09K 2211/1088* (2013.01); *C09K 2211/1092* (2013.01); *H01L 51/0003* (2013.01); *H01L 51/0005* (2013.01); *H01L 51/0072* (2013.01); *H01L 51/0073* (2013.01); *H01L 51/0081* (2013.01); *H01L 51/50* (2013.01); *H01L 51/5012* (2013.01); *H01L 51/5056* (2013.01); *H01L 51/5064* (2013.01); *H01L 51/5088* (2013.01); *Y02E 10/549* (2013.01)

(58) Field of Classification Search
None
See application file for complete search history.

(56) References Cited

U.S. PATENT DOCUMENTS

2011/0248246 A1* 10/2011 Ogita .................. C07D 333/76
257/40

* cited by examiner

*Primary Examiner* — Gregory D Clark
(74) *Attorney, Agent, or Firm* — Vorys, Sater, Seymour & Pease LLP; Mih Suhn Koh

(57) ABSTRACT

Provided is a compound for an EBL capable of improving the light emitting efficiency, stability and life span of a device, and an organic electric element and an electronic device using the same.

11 Claims, 1 Drawing Sheet

(51) Int. Cl.
*H05B 33/14* (2006.01)
*C07D 333/76* (2006.01)
*C07D 409/12* (2006.01)
*C07D 409/14* (2006.01)
*C09K 11/06* (2006.01)

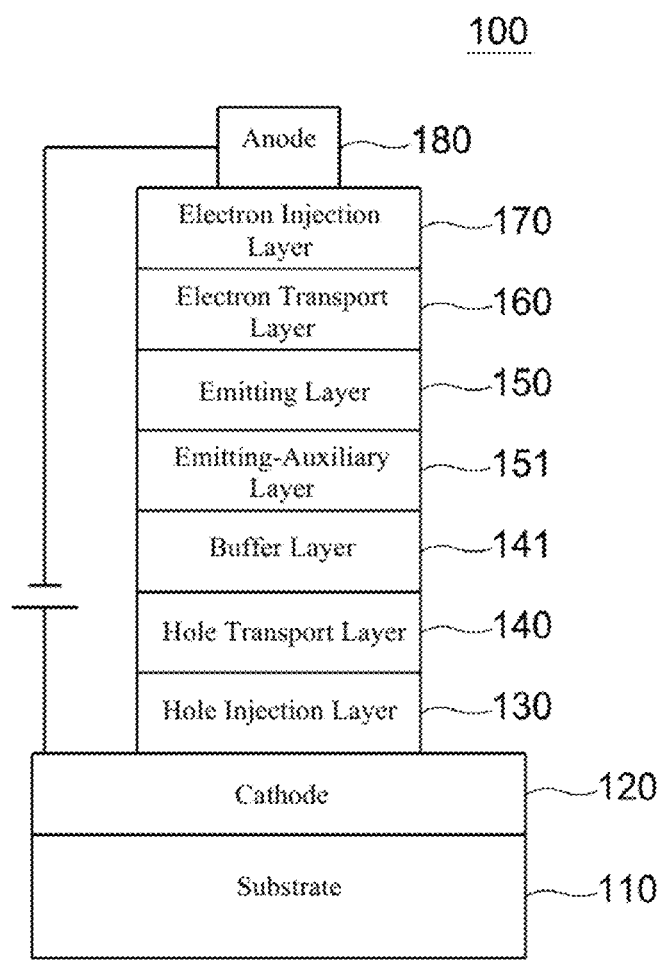

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATIONS

This application is a continuation of U.S. patent application Ser. No. 15/427,363, filed Feb. 8, 2017, which claims the benefit of priority from Korean Patent Application No. 10-2016-0015595, filed Feb. 11, 2016, the contents of each of which are incorporated herein by reference in its entirety.

TECHNICAL FIELD

The present invention relates to compound for organic electronic element, organic electronic element using the same, and an electronic device thereof.

BACKGROUND ART

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. Here, in many cases, the organic material layer may have a multi-layered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function.

The most problematic issues in an organic electric element are life span and efficiency, and the situation is such that this life span or efficiency issue must be solved as displays become larger and larger.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase.

However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective organic material layers is given.

Further, in order to solve the emission problem with a hole transport layer in a recent organic electric element, an emitting-auxiliary layer is present between the hole transport layer and a light emitting layer, and it is time to develop different emitting-auxiliary layers according to respective light emitting layers (R, G, B).

In general, an electron transferred from an electron transport layer to a light emitting layer and a hole transferred from a hole transport layer to the light emitting layer are recombined to form an exciton.

However, since materials to be used in the hole transport layer must have low HOMO values, they mostly have low T1 values, and on account of this, the exciton formed in the light emitting layer is transferred into the hole transport layer, which causes charge unbalance in the light emitting layer and thus are emitted at a hole transport layer interface.

The light emission at the hole transport layer interface has a problem in that color purity and efficiency are lowered and life span is shortened. Therefore, there is an urgent need to develop an emitting-auxiliary layer which has a high T1 values and the HOMO level of which is between the HOMO energy level of a hole transport layer and the HOMO energy level of a light emitting layer.

In addition, it is required to develop a hole injection layer material that retards penetration/diffusion of metal oxides from an anode electrode (ITO) into an organic material layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus there is an actual need to develop a material that is durable to such a deposition method, that is, a highly heat-resistant material.

In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, an emitting-auxiliary layer material or the like, by a stable and efficient material. However, such a stable and efficient organic material layer material for an organic electric element has not yet been fully developed. Accordingly, there is a continuous need to develop new materials for a hole transport layer or an emitting-auxiliary layer.

SUMMARY

In order to solve one or more of the above-mentioned problems occurring in background art, an aspect of the present invention is to provide a compound which allows an organic electric element to further improve high luminous efficiency, stability life span.

An object of the present invention is to provide a compound, an organic electric element and an electronic device using the same.

The present invention provides a compound represented by Formula (1) below and a composition for a hole transport layer and an emitting-auxiliary layer using the same and an organic electric element characterized in having the same.

Formula (1)

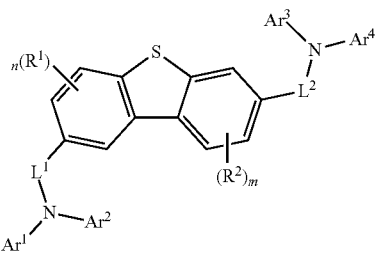

By using the compound according to the present invention, an organic electric element according to the present invention not only has high luminous efficiency, low driving voltage and high heat resistance and, but can also be significantly improved in color purity and life span.

BRIEF DESCRIPTION OF THE DRAWINGS

The FIGURE illustrates an example of an organic light emitting diode according to the present invention.

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It will be understood that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine, chlorine, bromine, or iodine.

Unless otherwise stated, the term "alkyl" or "alkyl group" as used herein has a single bond of 1 to 60 carbon atoms, and means saturated aliphatic functional radicals including a linear alkyl group, a branched chain alkyl group, a cycloalkyl group (alicyclic), a cycloalkyl group substituted with an alkyl, or an alkyl group substituted with a cycloalkyl.

Unless otherwise stated, the term "haloalkyl" or "halogen alkyl" as used herein includes an alkyl group substituted with a halogen.

Unless otherwise stated, the term "heteroalkyl" as used herein means alkyl substituted one or more of carbon atoms consisting of an alkyl with hetero atom.

Unless otherwise stated, the term "alkenyl" or "alkynyl" as used herein has, but not limited to, double or triple bonds of 2 to 60 carbon atoms, and includes a linear alkyl group, or a branched chain alkyl group, Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "alkenoxyl group", "alkenoxy group", "alkenyloxy group" or "alkenyloxy group" as used herein means an oxygen radical attached to an alkenyl group, but not limited to, and has 2 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. Examples of "aryl group" may include a phenyl group, a biphenyl group, a fluorene group, or a spirofluorene group.

The prefix "aryl" or "Ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "heteroalkyl" as used herein means alkyl containing one or more of hetero atoms. Unless otherwise stated, the term "heteroaryl group" or "heteroarylene group" as used herein means, but not limited to, a C2 to C60 aryl or arylene group containing one or more of hetero atoms, includes at least one of monocyclic and polycyclic rings, and may also be formed in conjunction with an adjacent group.

Unless otherwise stated, the term "heterocyclic group" as used herein contains one or more of hetero atoms, but not limited to, has 2 to 60 carbon atoms, includes at least one of monocyclic and polycyclic rings, and may include hetero alicyclic and hetero aromatic group. Also, the heterocyclic group may also be formed in conjunction with an adjacent functional group.

Unless otherwise stated, the term "hetero atom" as used herein represents N, O, S, P, and Si.

Also, the term "heterocyclic group" may include a ring containing $SO_2$ instead of carbon consisting of cycle. For example, "heterocyclic group" includes compound below.

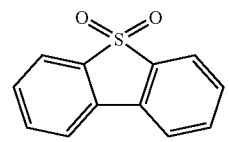 [SMILES: O=S1(=O)c2ccccc2-c2ccccc21]

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more of hetero atoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted" as used herein means that substitution is substituted by at least one substituent selected from the group consisting of, but not limited to, deuterium, halogen, an amino group, a nitrile group, a nitro group, a $C_2$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

Otherwise specified, the Formulas used in the present invention are as defined in the index definition of the substituent of the following Formula:

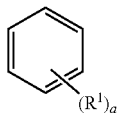

wherein, when a is an integer of zero, the substituent $R^1$ is absent, when a is an integer of 1, the sole substituent $R^1$ is linked to any one of the carbon constituting the benzene ring, when a is an integer of 2 or 3, the substituent $R^1$s may be the same and different, and are linked to the carbon of the benzene ring as follows, when a is an integer of 4 to 6, and is linked to the benzene ring in a similar manner, whereas hydrogen atoms linked to carbon constituents of the benzene ring are not represented as usual.

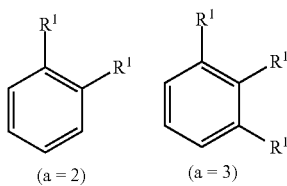

Hereinafter, a compound and an organic electric element comprising the same according to an aspect of the present invention will be described.

According to a specific example, the present invention provides the compound represented Formula (1) below.

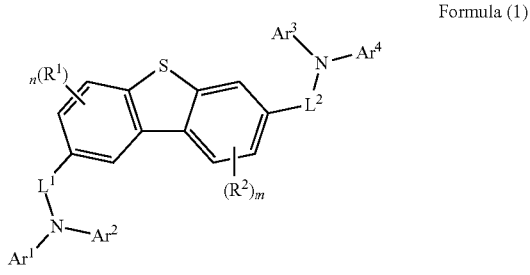

Formula (1)

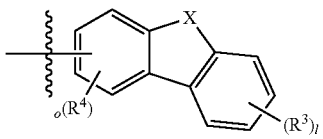

Formula (1-1)

{in Formula (1) and Formula (1-1) above,

1) $Ar^1$, $Ar^2$, $Ar^3$ and $Ar^4$ are each independently selected from the group consisting of a halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group; a $C_2$-$C_{20}$ alkynyl group; a $C_1$-$C_{30}$ alkoxyl group, a $C_6$-$C_{30}$ aryloxy group; and -L'-N($R_a$)($R_b$) or may combine to form an aromatic ring or a hetero-aromatic ring by condensation neighboring groups with rings, but at least one may be the substituent represented Formula(1-1) above, 2) $L^1$ and $L^2$ may be selected from the group consisting of a single bond; a $C_6$-$C_{60}$ arylene group; a fluorenylene group; a $C_2$-$C_{60}$ hetero arylene group including at least one hetero atom of O, N, S, Si or P, 3) l is an integer of 0 to 4, m, n and o are an integer of 0 to 3, 4) $R^1$, $R^2$, $R^3$ and $R^4$ are each independently selected from the group consisting of hydrogen; deuterium; halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R_a$)($R_b$); and a plurality of $R^1$ and/or a plurality of $R^2$ and/or a plurality of $R^3$ an/ord a plurality of $R^4$ may combine to each other to form a ring, when $R^1$ and/or $R^2$ is plural, and/or when $R^3$ and/or $R^4$ are plural, 5) X is O or S, 6) L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{20}$ heterocyclic, and the $R_a$ and $R_b$ may be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P.

(where, aryl group, fluorenyl group, arylene group, heterocyclic group, fused ring group may be substituted by one or more of substituents selected from the group consisting of deuterium; halogen; a silane group; a siloxan group a boron group; a germanium group; a cyano group; a nitro group; -L'-N($R_a$)($R_b$); a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted by deuterium; fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group; and also may combine to each other to form a ring, wherein 'ring' means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.)}

In addition, according to the present invention, the compound represented by Formula (1) above includes any one of compounds of Formula (2) or Formula (3) below.

(In Formula (2) and Formula (3) above, $R^1$, $R^2$, $R^3$, $R^4$, l, m, n, o, $Ar^1$, $Ar^2$, $Ar^3$, $Ar^4$, $L^1$, $L^2$, X are as defined in Formula (1) above.)

In addition, the present invention provides the compound represented any one of compounds of Formula (4) to Formula (9) below.

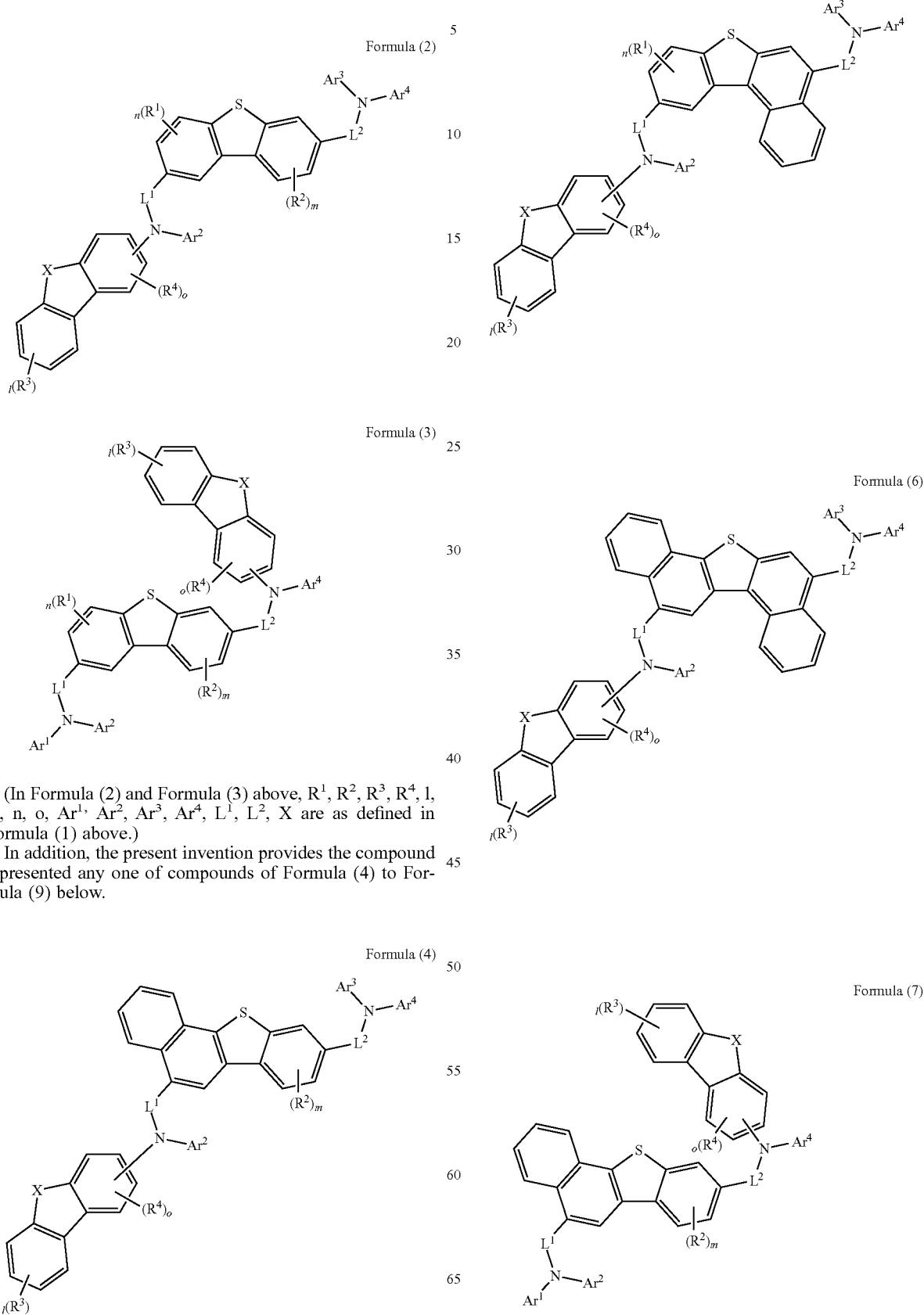

Formula (8)
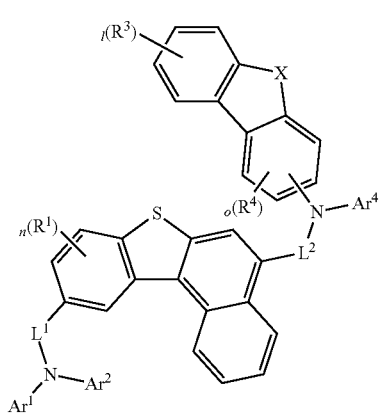
Formula (9)
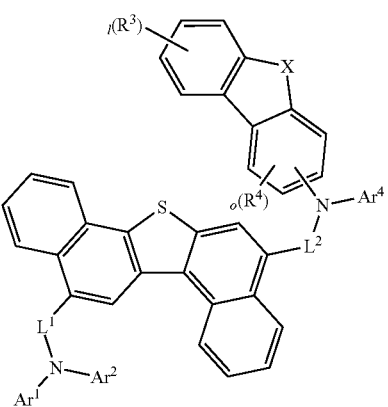
(In Formula (4) to Formula (9) above, $R^1$, $R^2$, $R^3$, $R^4$, l, m, n, o, $Ar^1$, $Ar^2$, $Ar^3$, $Ar^4$, $L^1$, $L^2$, X are as defined in Formula (1) above.)
According to the present invention, the compound represented by Formula(1) above includes one of the compounds below
P-1
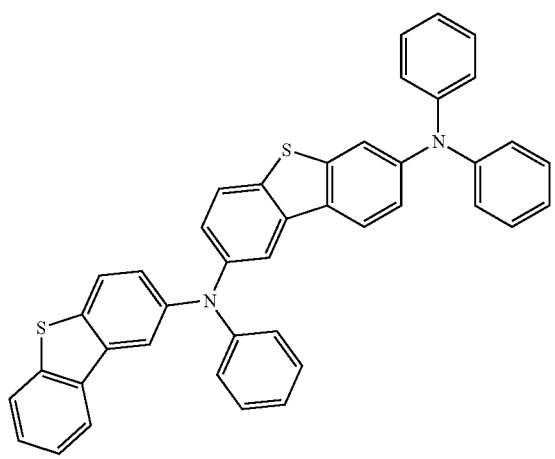
P-2
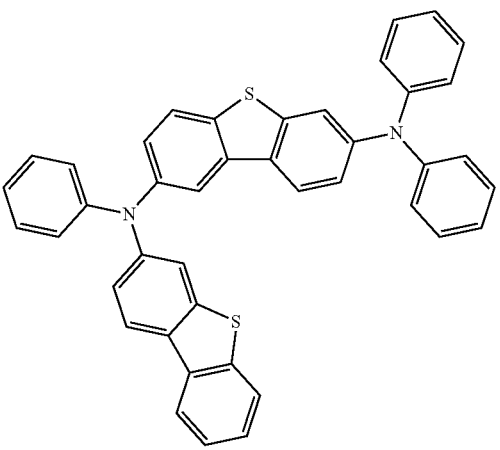
P-3
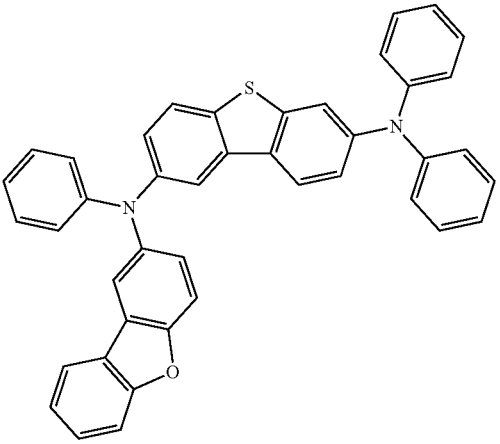
P-4
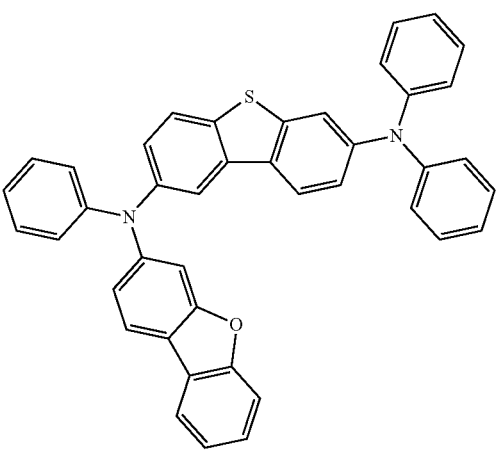

P-5
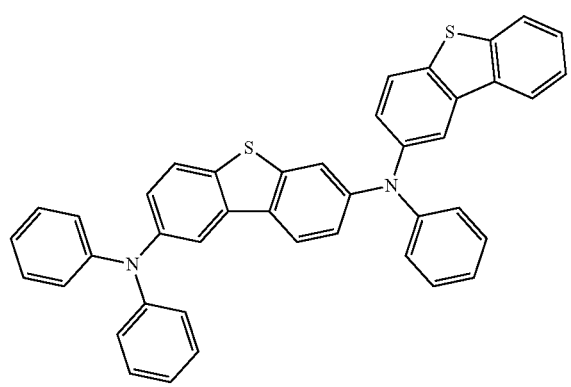
P-8
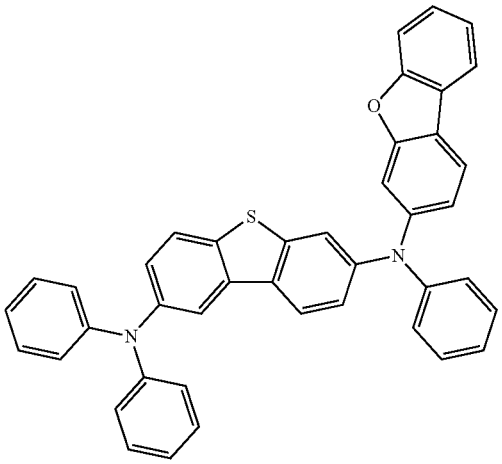
P-6
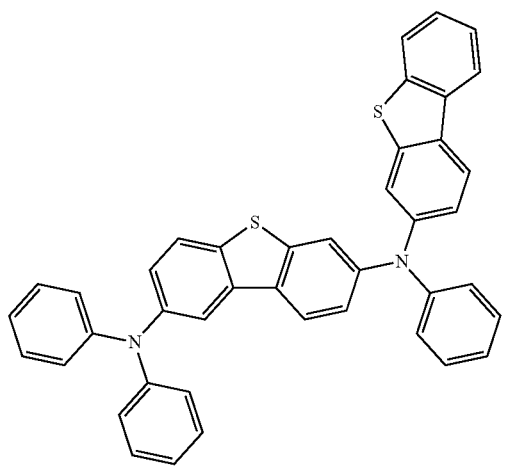
P-9
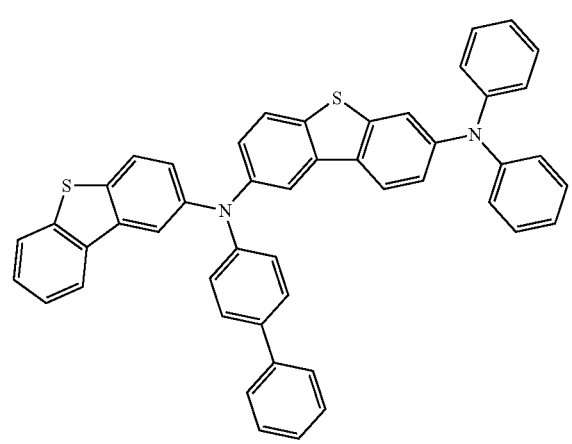
P-7
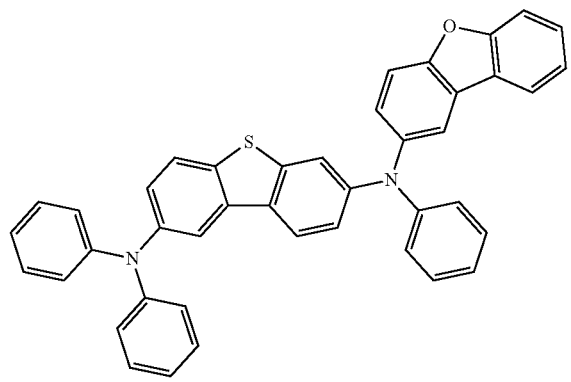
P-10
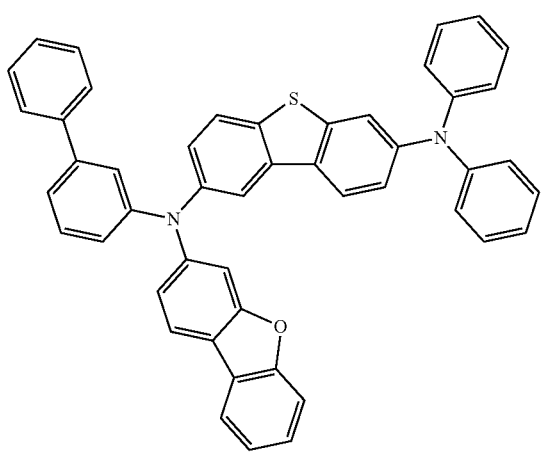

P-11
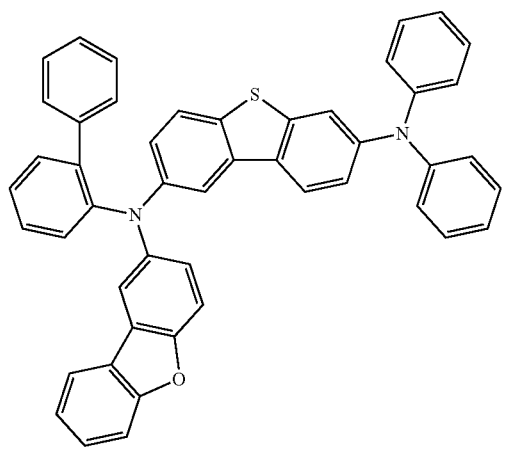
P-12
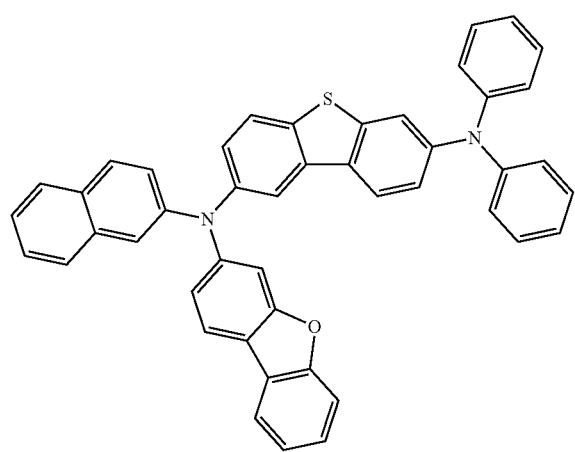
P-13
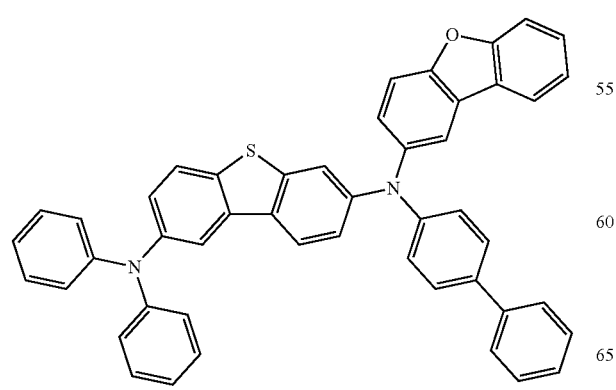
P-14
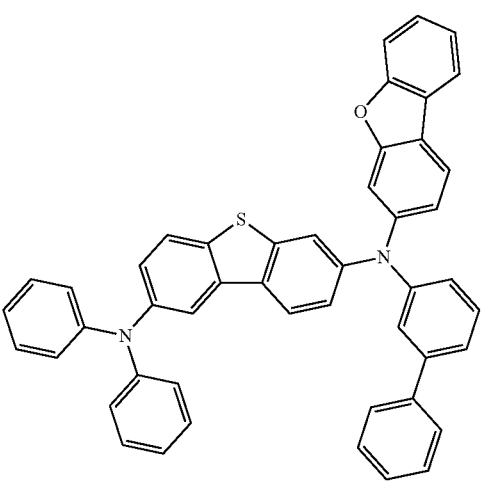
P-15
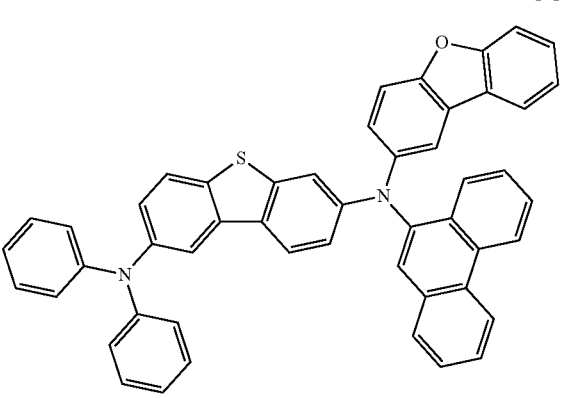
P-16
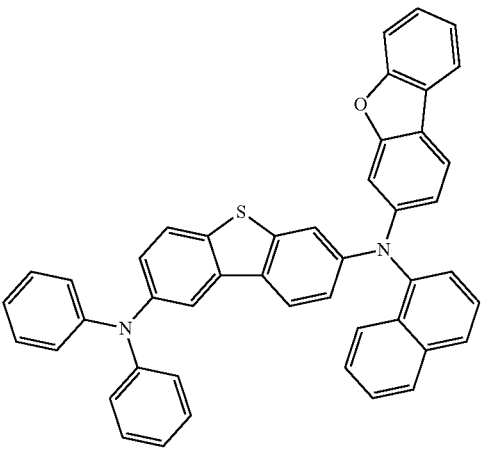

P-17
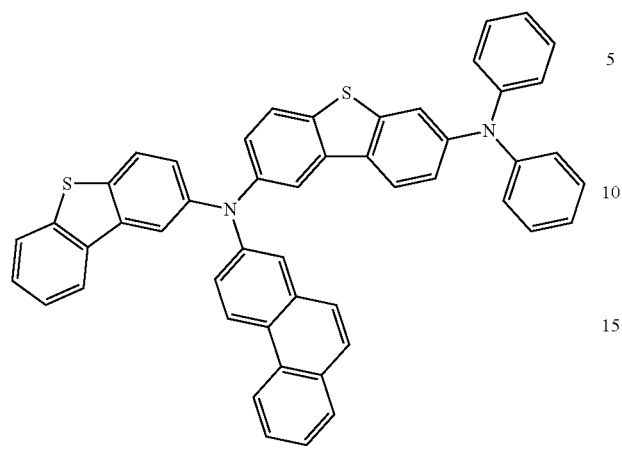
P-20
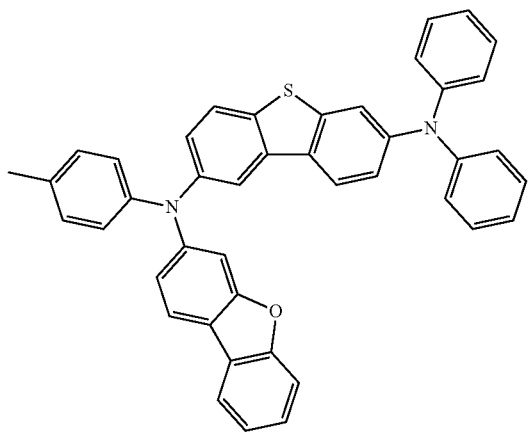
P-18
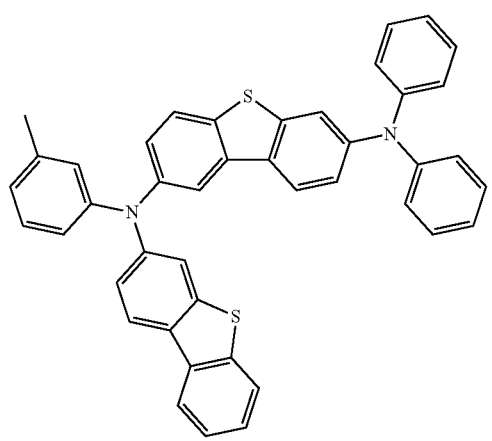
P-21
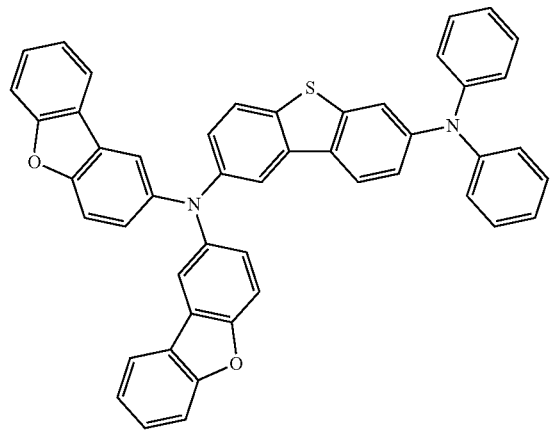
P-19
P-22
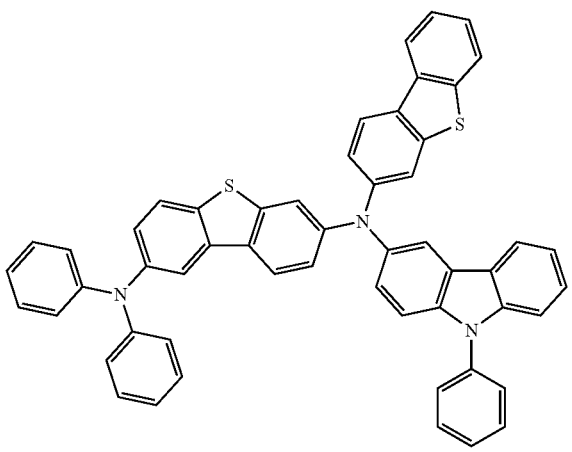

P-23
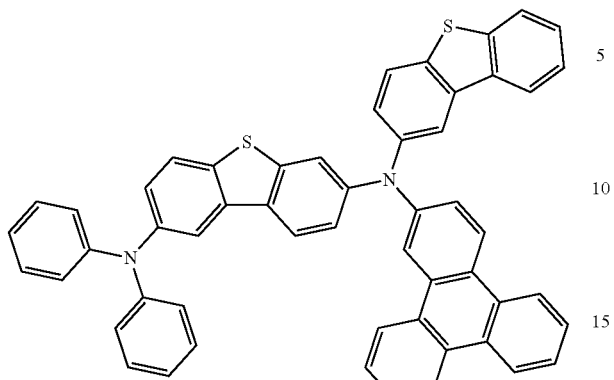
P-26
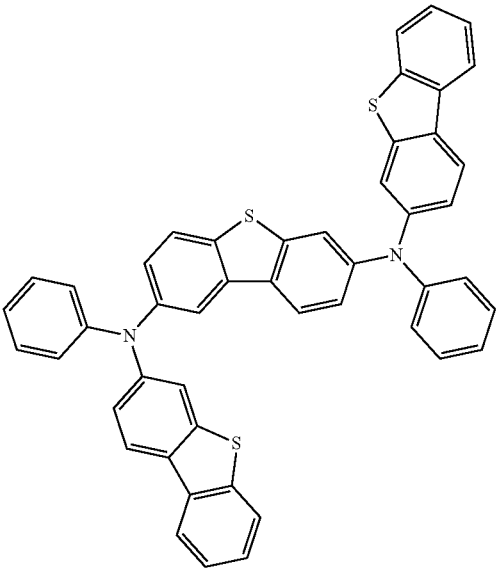
P-24
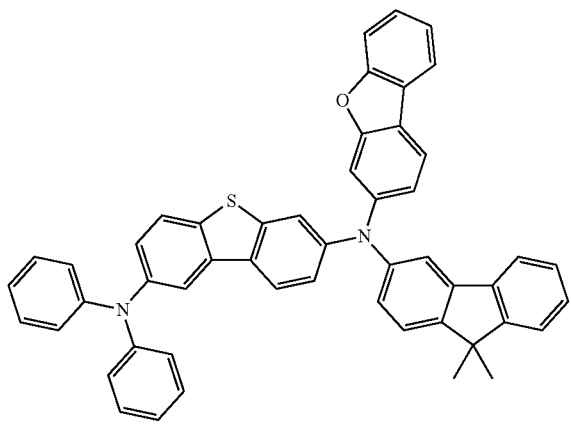
P-27
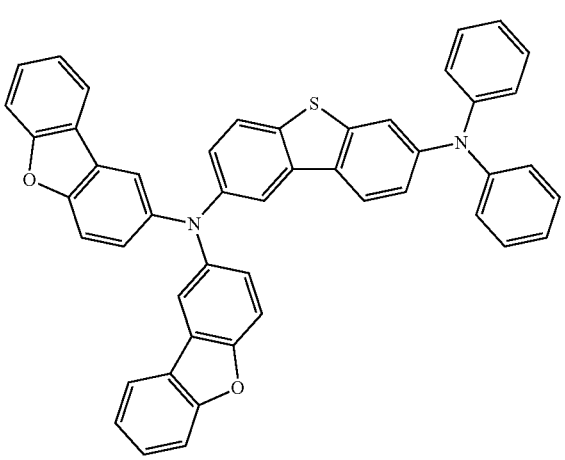
P-25
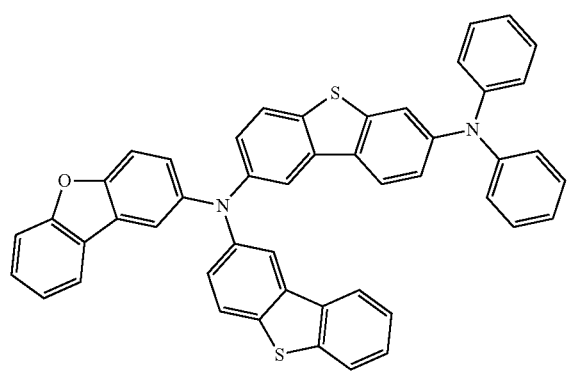
P-28
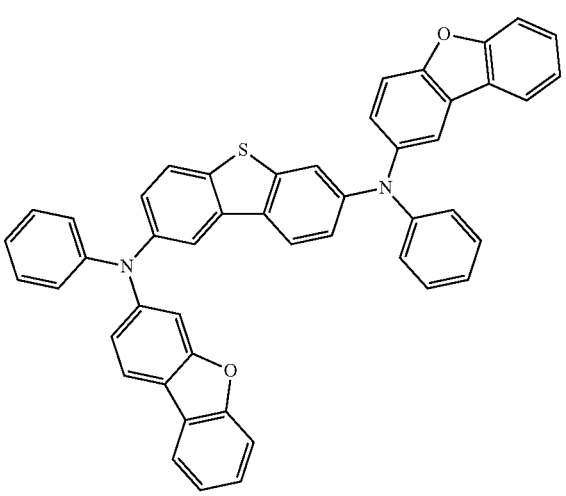

-continued
P-29
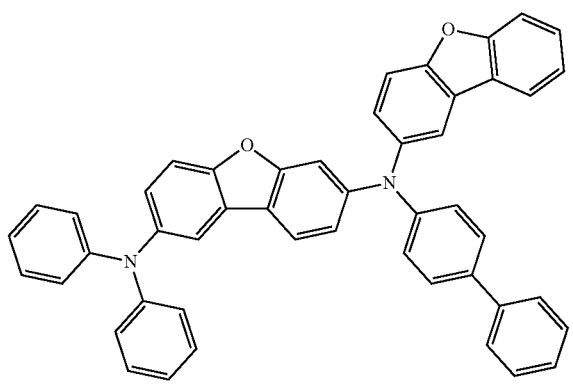
P-30
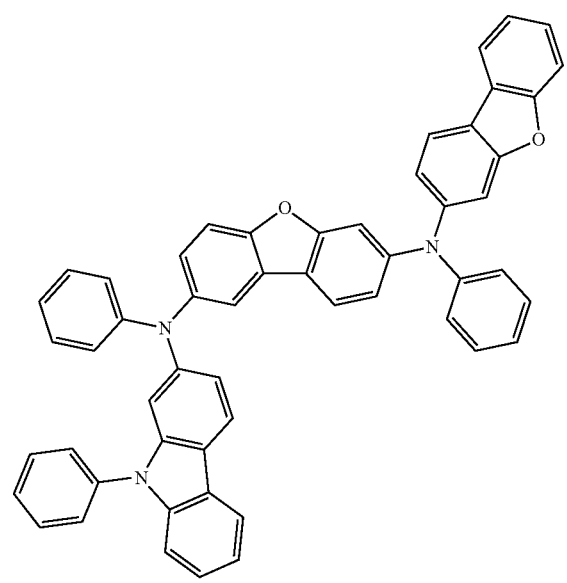
P-31
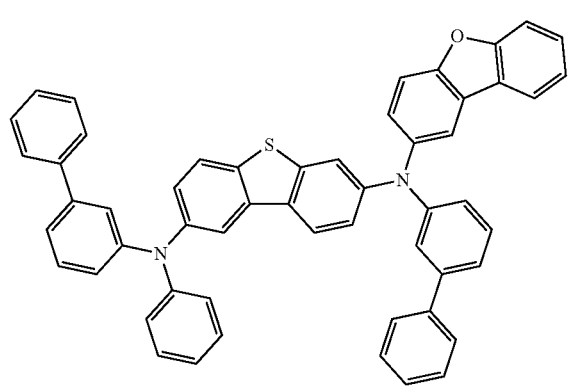
-continued
P-32
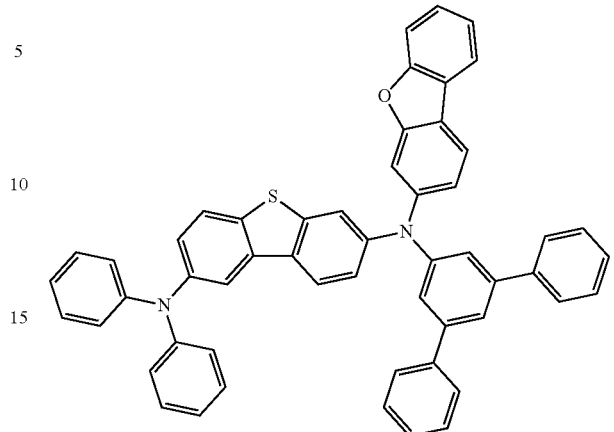
P-33
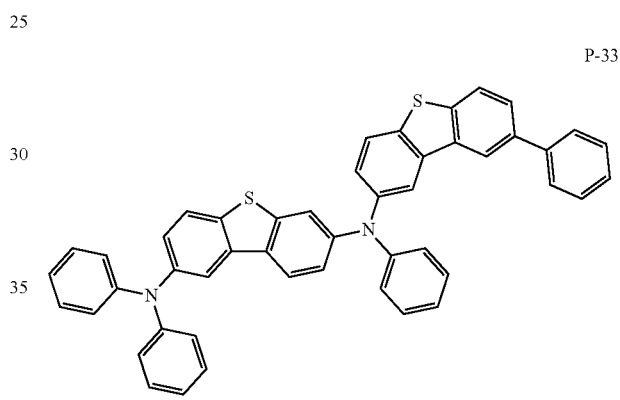
P-34
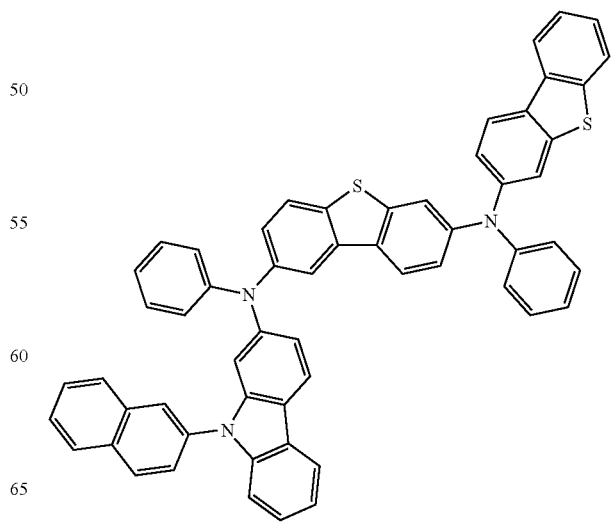

P-35
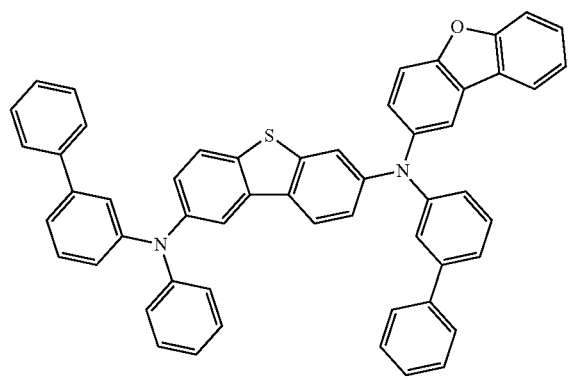
P-38
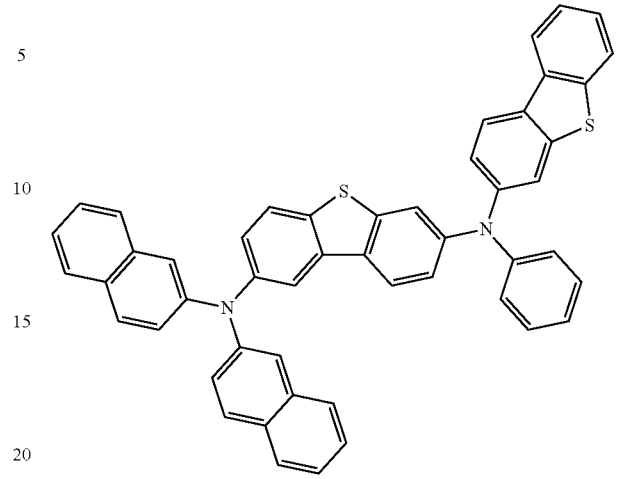
P-36
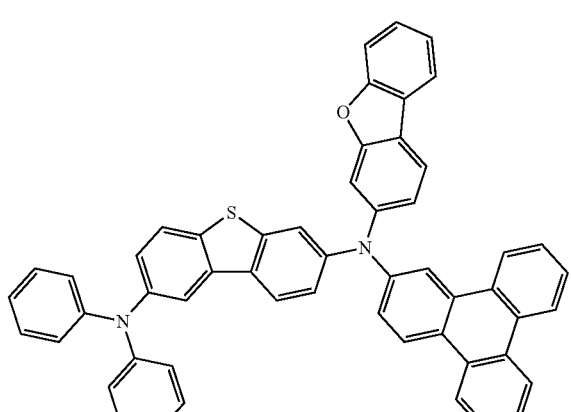
P-39
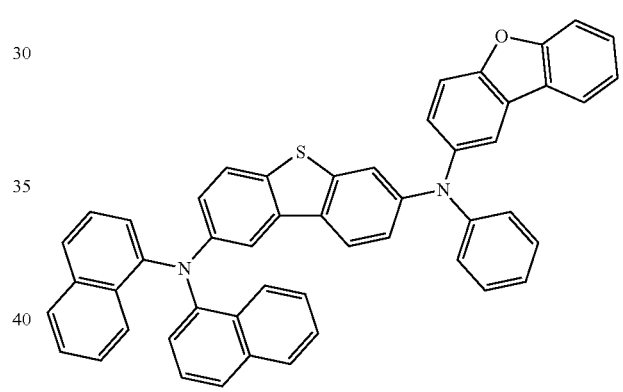
P-37
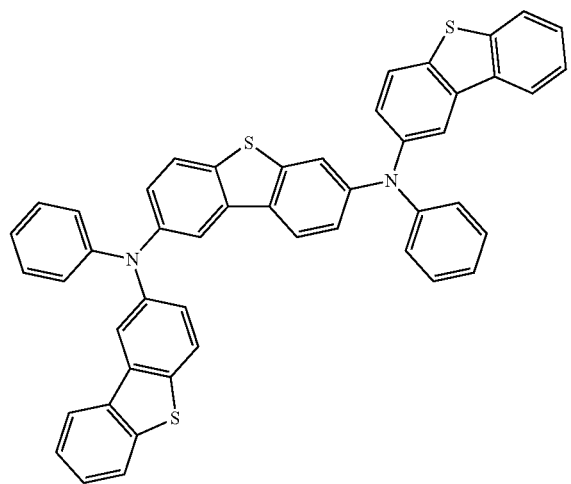
P-40

P-41
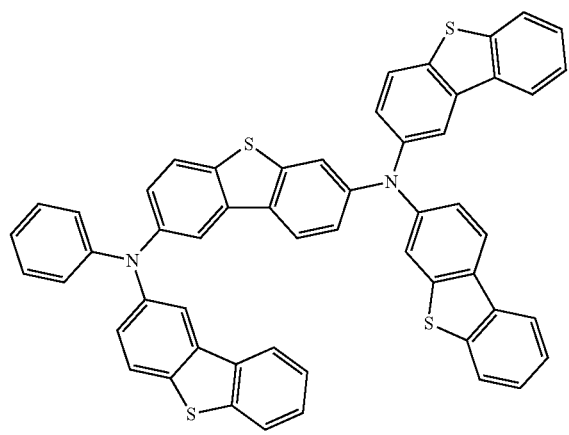
P-42
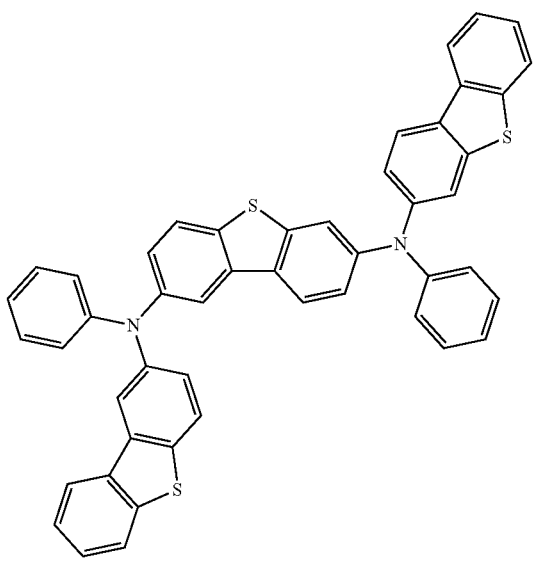
P-43
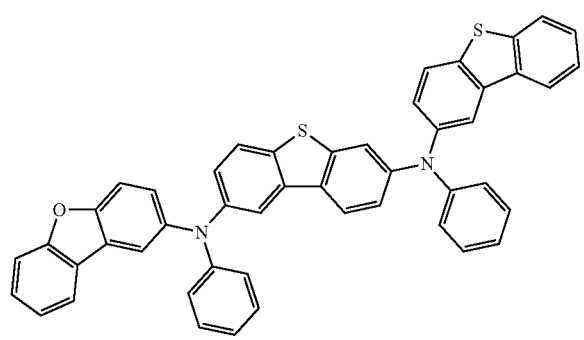
P-44
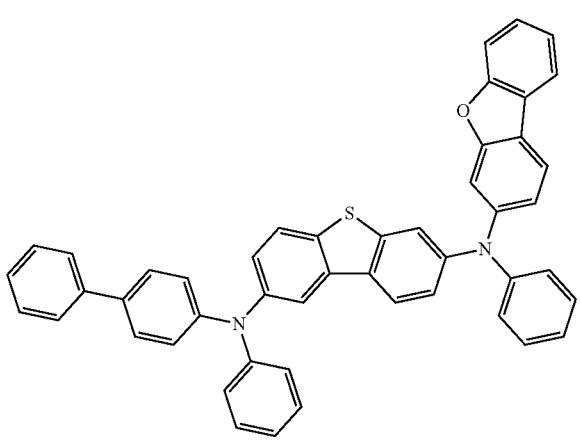
P-45
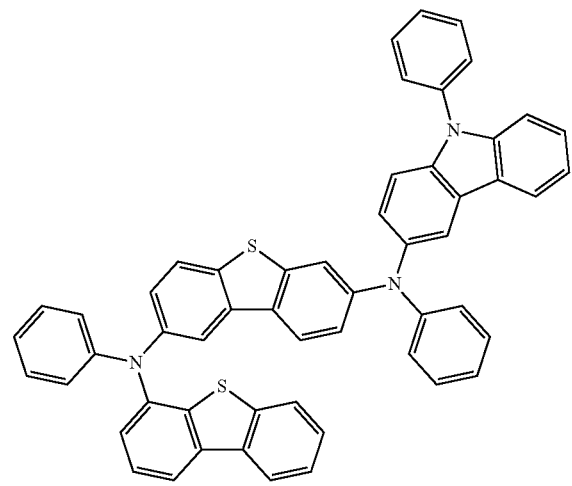
P-46
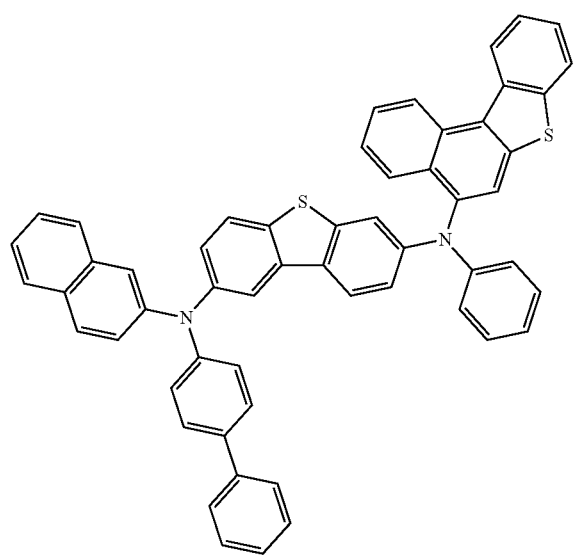

-continued
P-47
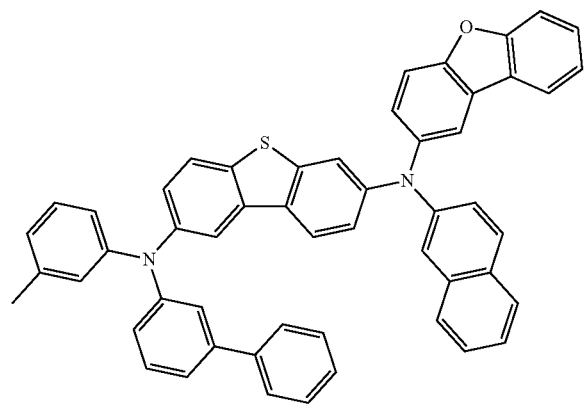
P-48
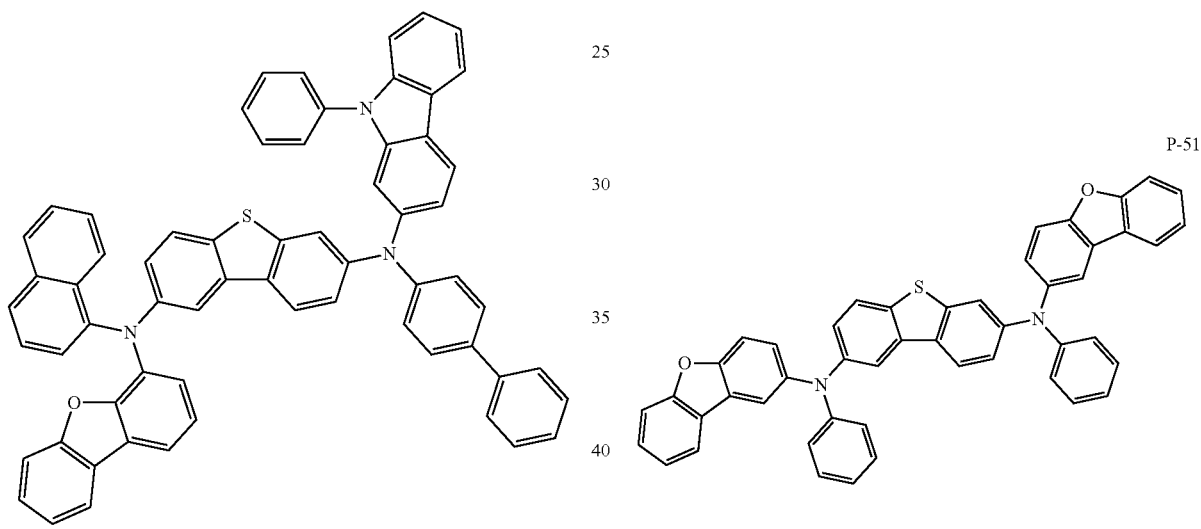
P-49
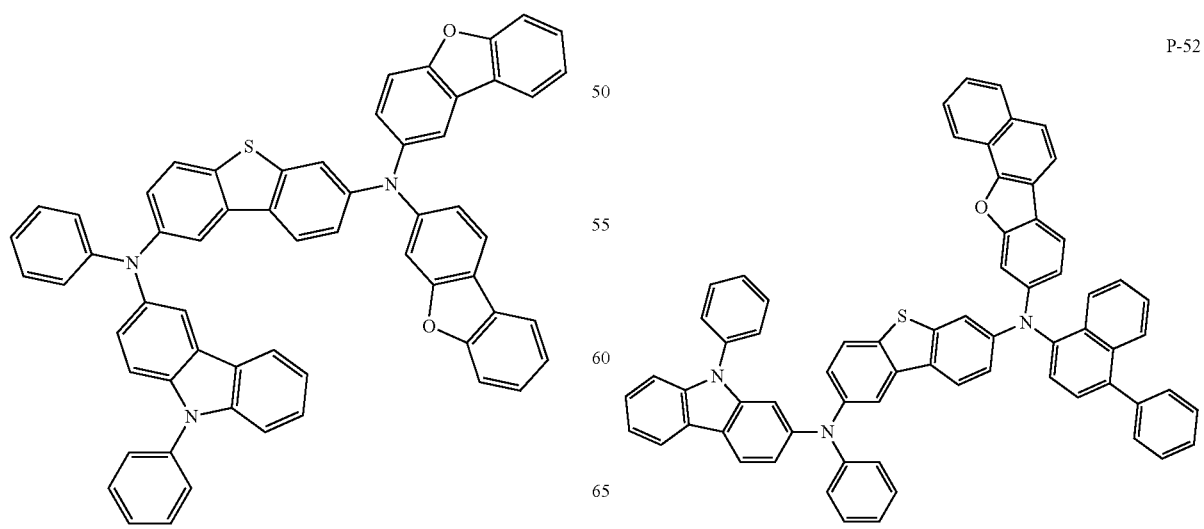
-continued
P-50
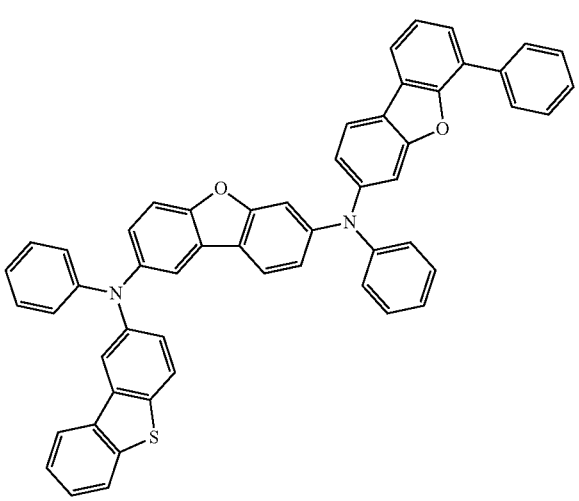
P-51
P-52

-continued
P-53
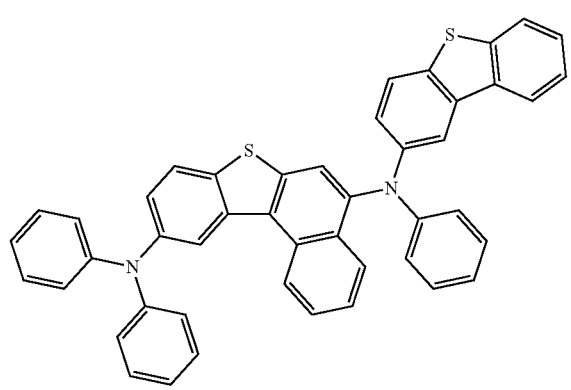
P-54
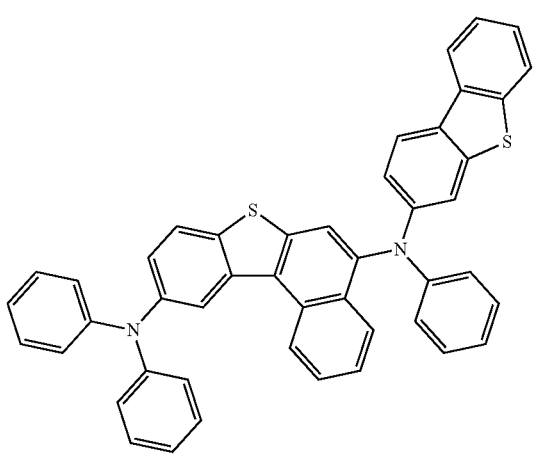
P-55
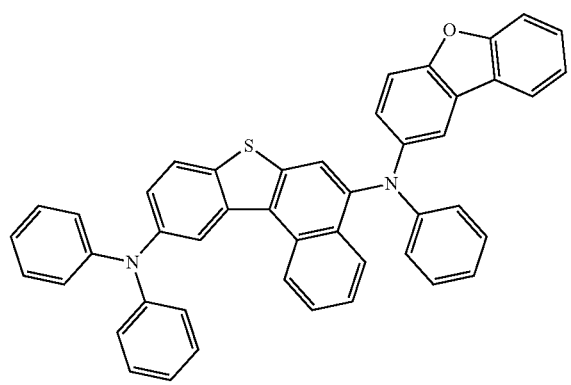
-continued
P-56
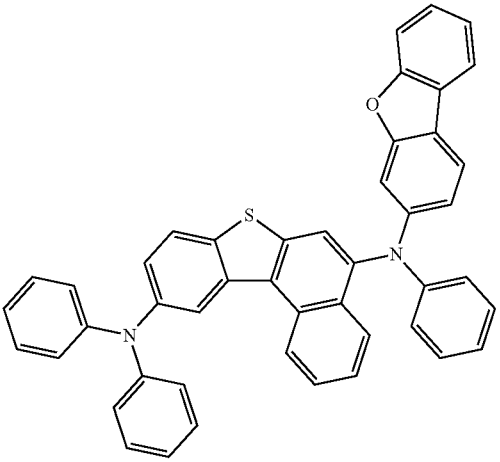
P-57
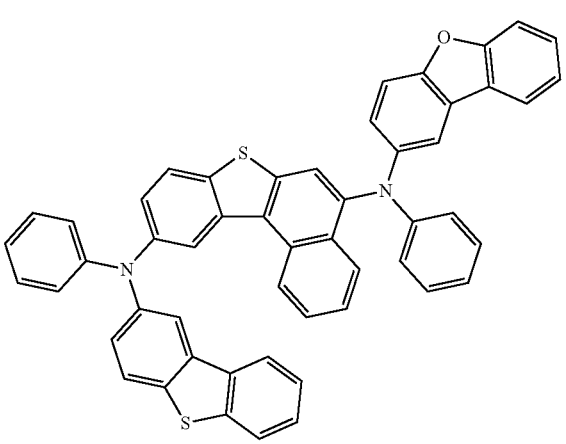
P-58
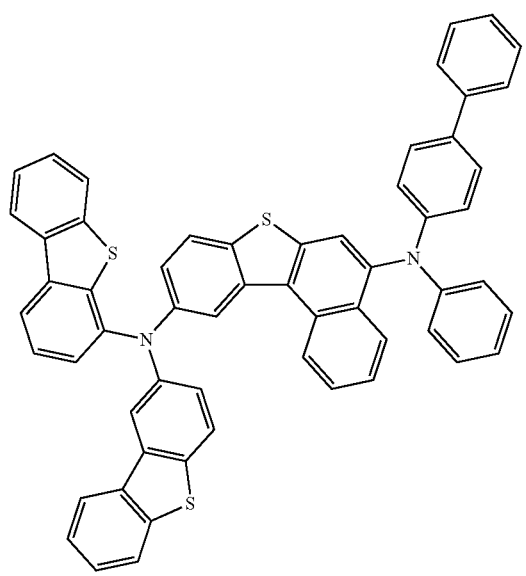

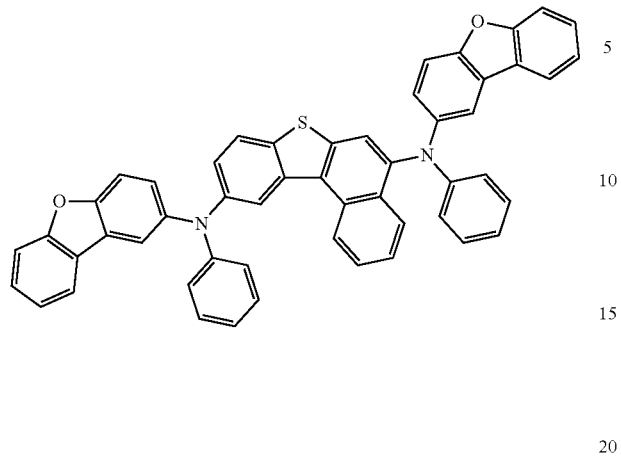
P-59
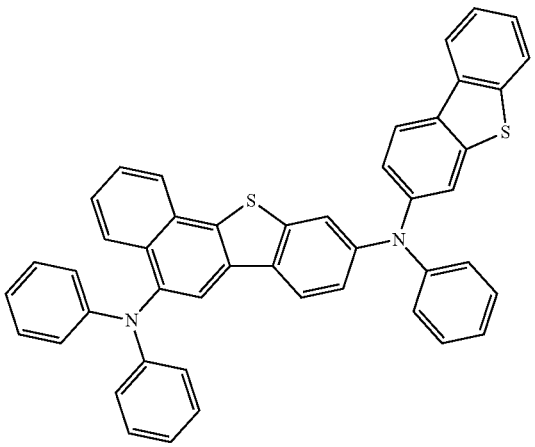
P-62
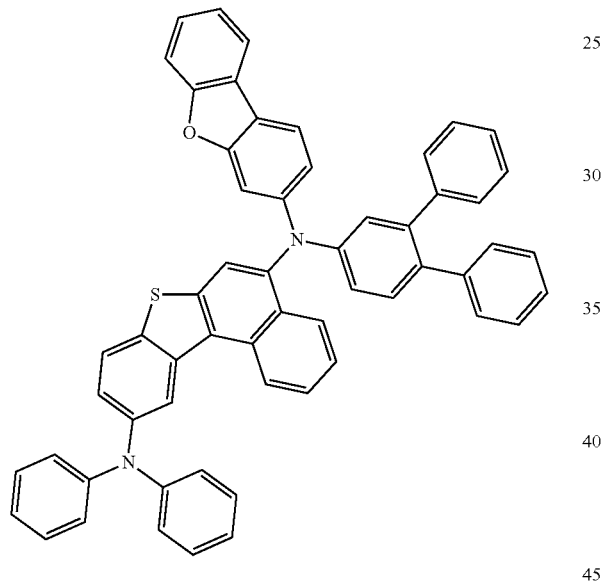
P-60
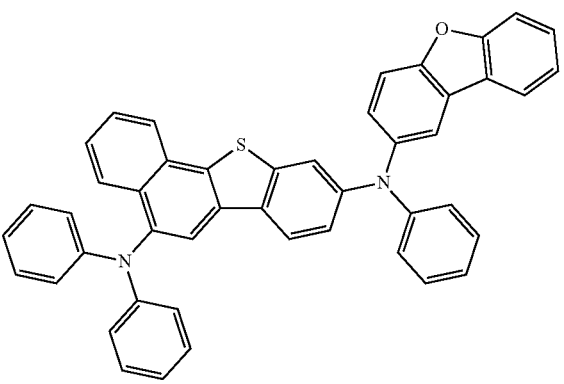
P-63
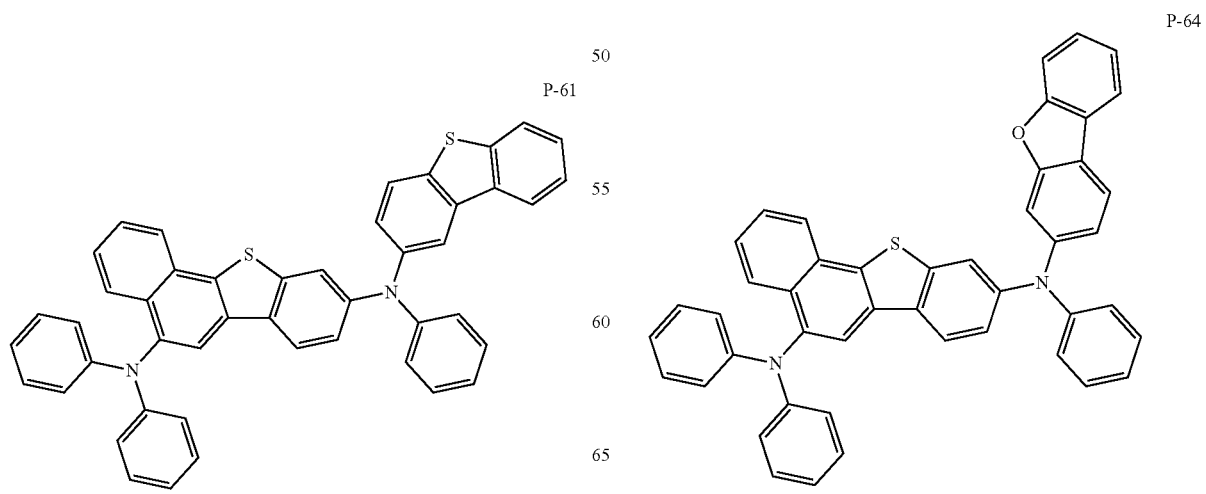
P-61
P-64

-continued
P-65
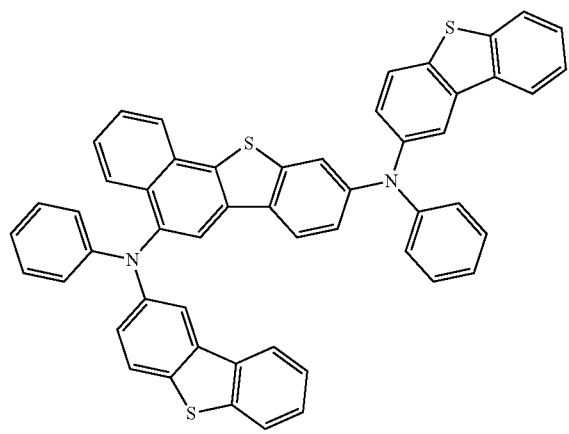
P-66
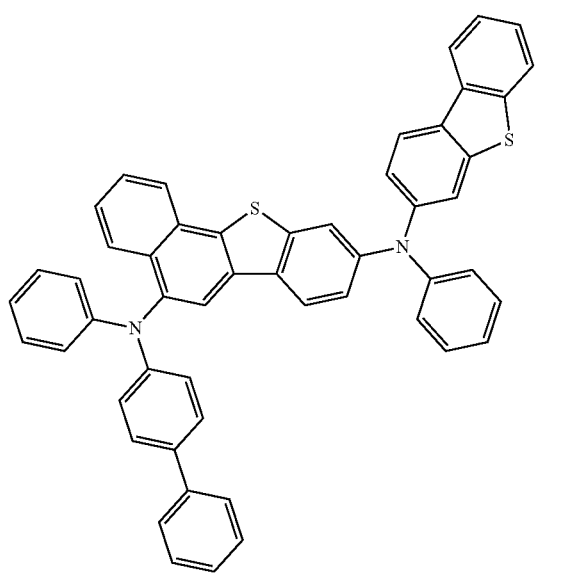
P-67
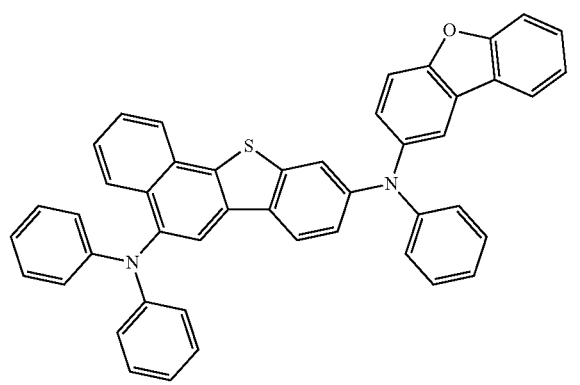
P-68
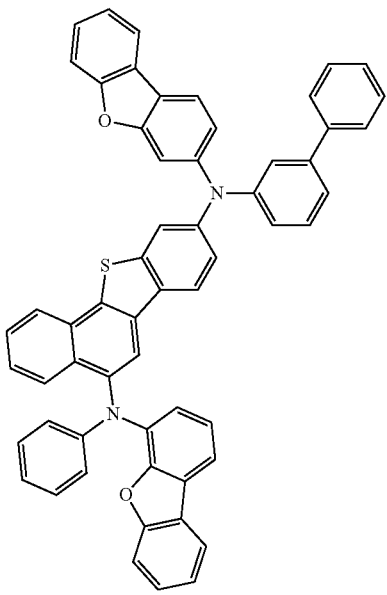
P-69
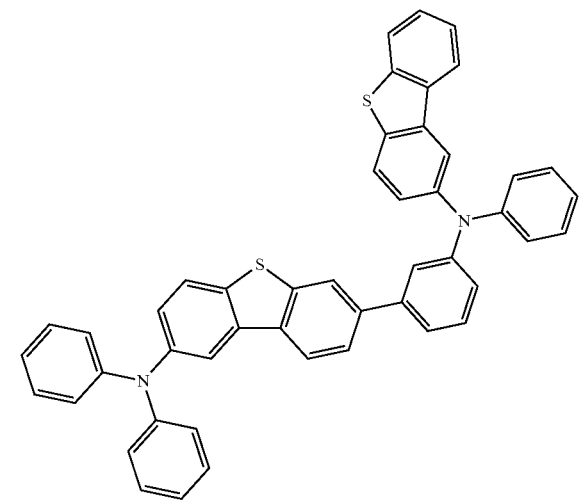
P-70
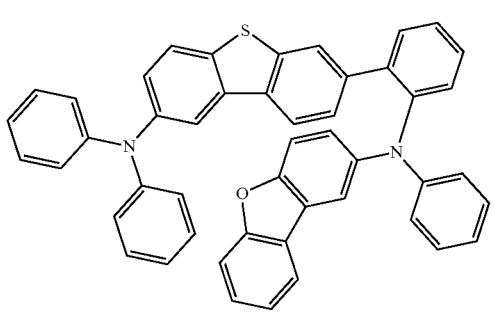

-continued
P-71
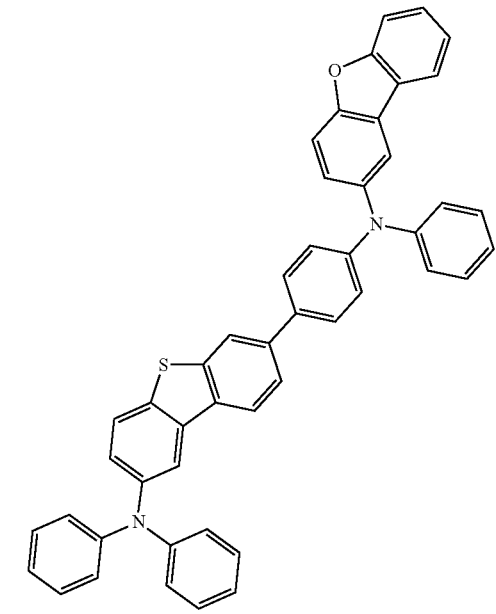
P-72
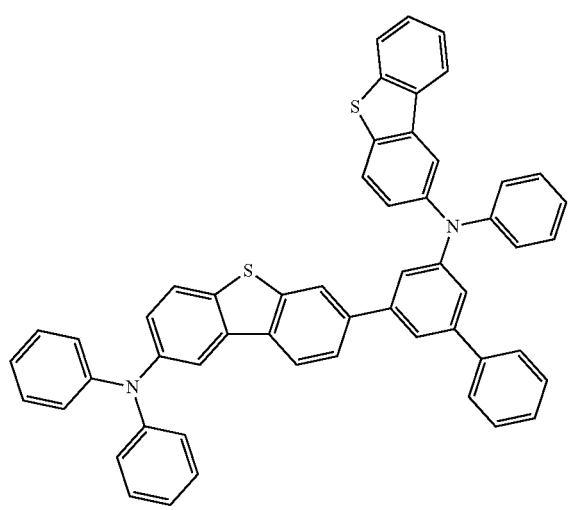
P-73
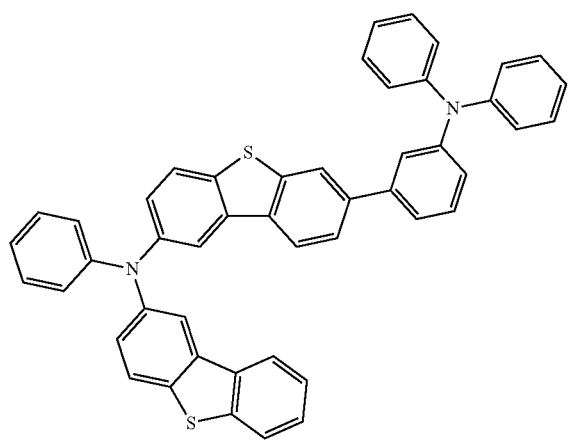
-continued
P-74
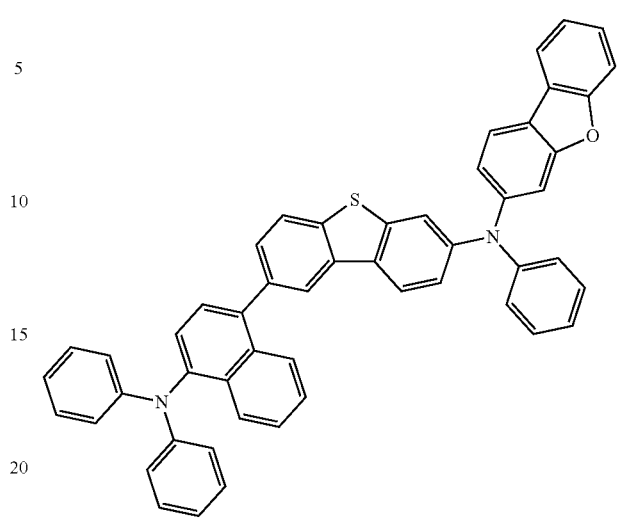
P-75
P-76
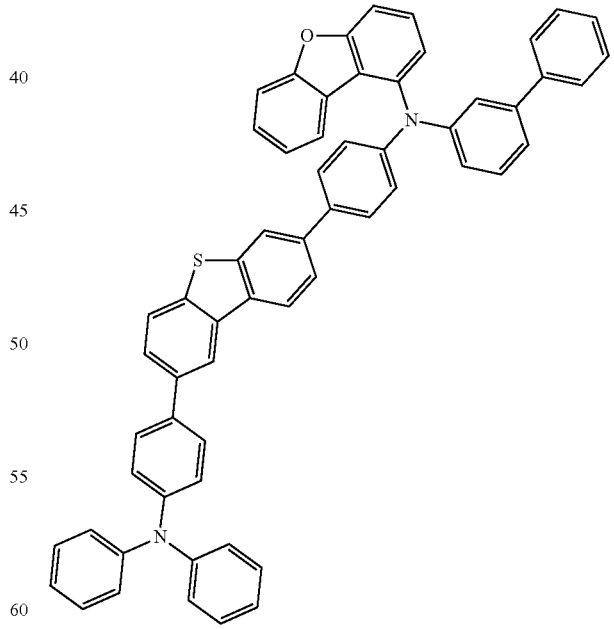
Referring to the FIGURE, an organic electric element (100) according to the present invention includes a first electrode (120) formed on a substrate (110), a second electrode (180), and an organic material layer between the first electrode (120) and the second electrode (180), which contains the compound represented by Formulas 1. Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may include a hole injection layer (130), a hole transport layer (140), a emitting layer (150), an electron transport layer (160), and an electron injection layer (170) formed in sequence on the first electrode (120). Here, the layers included in the organic material layer, except the emitting layer (150), may not be formed. The organic material layer may further include a hole blocking layer, an electron blocking layer, an emitting-auxiliary layer (151), a buffer layer (141), etc., and the electron transport layer (160) and the like may serve as the hole blocking layer.

Although not shown, the organic electric element according to the present invention may include a protective layer formed on at least one side of the first and second electrodes, which is a side opposite to the organic material layer.

This implies that depending on the type and position of a substituent to be attached, a band gap, electrical properties, interfacial properties, and the like may greatly vary even in the same indole core. The selection of core and the combination of the combined sub-substituents thereof is very important, especially this is because long life span and high efficiency can be simultaneously achieved when an optimal combination of energy levels and T1 values, inherent material properties (mobility, interfacial properties, etc.), and the like among the respective organic material layers is given.

The organic electric element according to an embodiment of the present invention may be manufactured using a PVD (physical vapor deposition) method. For example, the organic electric element may be manufactured by depositing a metal, or a conductive metal oxide, or a mixture thereof on the substrate (110) to form the anode (120), forming the organic material layer including the hole injection layer (130), the hole transport layer (140), the emitting layer (150), the electron transport layer (160), and the electron injection layer (170) thereon, and then depositing a material, which can be used as the cathode (180), thereon.

The present invention provides the organic electric element characterized in that can comprise a first electrode; a second electrode; and an organic material layer disposed between the first electrode and the second electrode. The organic material layer can comprise the compound represented by Formula 1.

In addition, the present invention may further include a light efficiency enhancing layer formed on at least one of the opposite side to the organic material layer among one side of the first electrode, or one of the opposite side to the organic material layer among one side of the second electrode.

Also, the present invention provides the organic electric element characterized in that the organic material layer is formed by one of a spin coating process, a nozzle printing process, an inkjet printing process, a slot coating process, a dip coating process or a roll-to-roll process, and comprise the compounds above as an electron transport material In another specific examples of the invention, the present invention provides the organic electric element characterized in that the mixture of the same or different kinds of compounds represented Formula (1) is used in the organic material layer Also, the present invention provides an organic electric element that includes a hole injection layer, a hole transport layer, an emitting layer or an emitting-auxiliary layer containing one or more of the compound represented by Formula 1 above.

More specially, the present invention provides an organic electric element that includes the compound represented by Formula 1 above in a hole transport layer or an emitting-auxiliary layer in the organic material layer The present invention also provides an electronic device including a display device including the organic electric element; and a control part driving the display apparatus.

According to another aspect, the present invention provides an electronic device characterized in that the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula (1) according to the present invention and preparation examples of an organic electric element will be described in detail by way of example. However, the following examples are only for illustrative purposes and are not intended to limit the following examples of the invention.

SYNTHESIS EXAMPLE

The final product represented by Formula (1) according to the present invention can be synthesized by reaction between Sub 1 and Sub 2 as illustrated in the following Reaction Scheme 1.

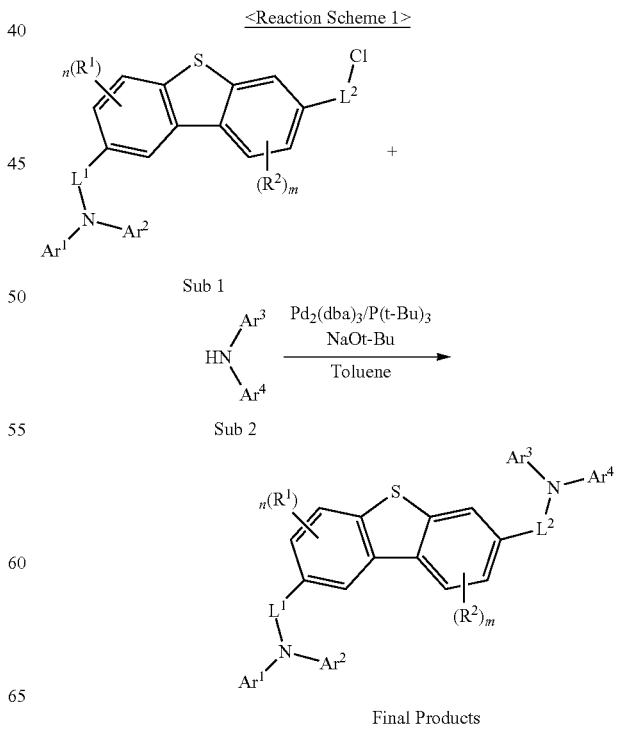

Final Products

Synthesis Examples of Sub 1

Sub 1 of Reaction Scheme 1 can be synthesized according to, but not limited to, the reaction path of the following Reaction Scheme 2.

<Reaction Scheme 2>

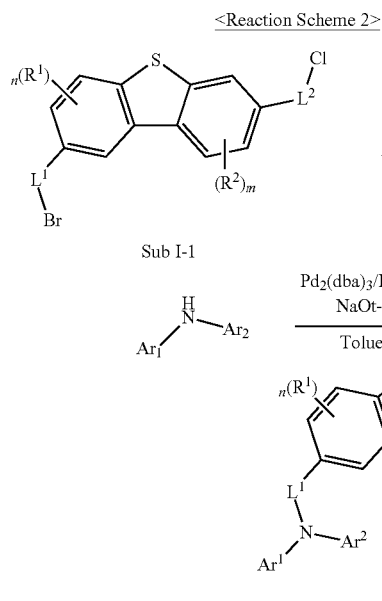

Examples of synthesizing specific compounds belonging to Sub 1 are as follows.

Synthesis Examples of Sub 1-1

<Reaction Scheme 3>

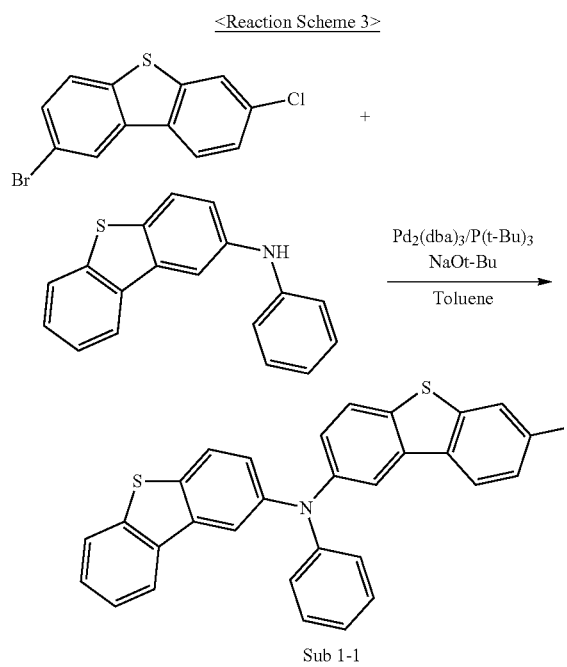

(1) Synthesis of Sub 1-1

S2-Bromo-7-chlorodibenzo[b,d]thiophene(15 g, 0.05041 mol), N-phenyldibenzo[b,d]thiophen-2-amine(13.8 g, 0.05041 mol), Pd$_2$(dba)$_3$ (1.38 g, 0.0015 mol), (t-Bu)$_3$P (1.2 mL, 0.0030 mol), NaOt-Bu (14.5 g, 0.151 mol) were dissolved in anhydrous Toluene(180 mL), followed by reaction for 4 hours.

Upon completion of the reaction, the purity of the product was increased by chromatography and was carried out to obtain 20.02 g of Sub 1-1 (yield: 81%).

2. Synthesis Examples of Sub 1-5

<Reaction Scheme 4>

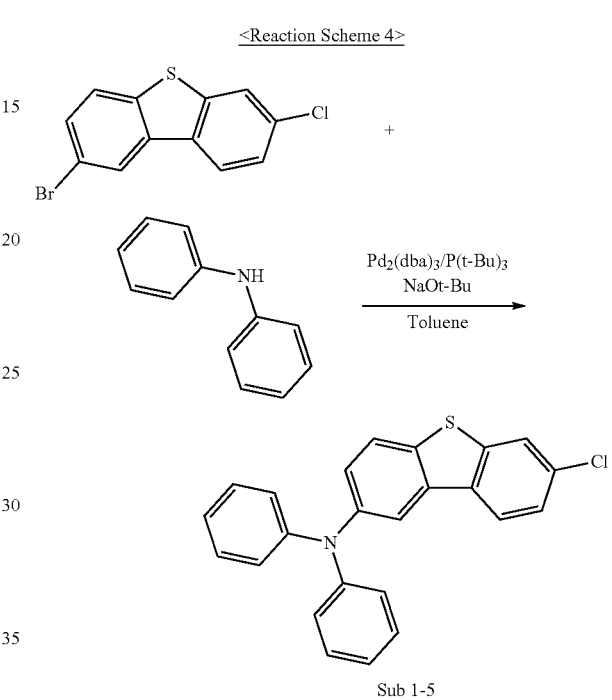

(1) Synthesis of Sub 1-5

Synth2-Bromo-7-chlorodibenzo[b,d]thiophene (100 g, 0.336 mol), diphenylamine (56.9 g, 0.3360 mol), Pd$_2$(dba)$_3$ (9.23 g, 0.01 mol), (t-Bu)$_3$P (8.2 mL, 0.02 mol), NaOt-Bu (96.9 g, 1.000 mol) were dissolved in anhydrous Toluene (1120 mL), and the same procedure as described in the synthesis method of Sub 1-1 above was carried out to obtain 80 g of Sub 1-5 (yield: 62%).

3. Synthesis Examples of Sub 1-32

<Reaction Scheme 5>

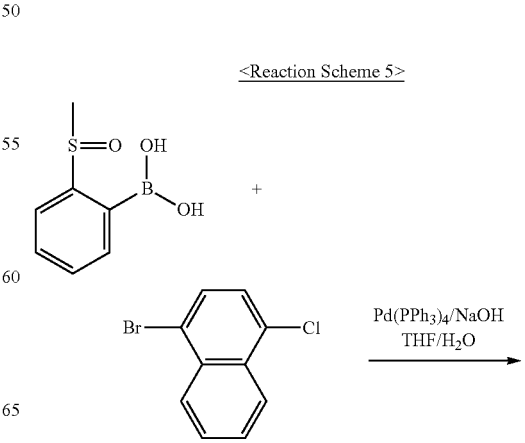

4. Synthesis Examples of Sub 1-37

<Reaction Scheme 6>

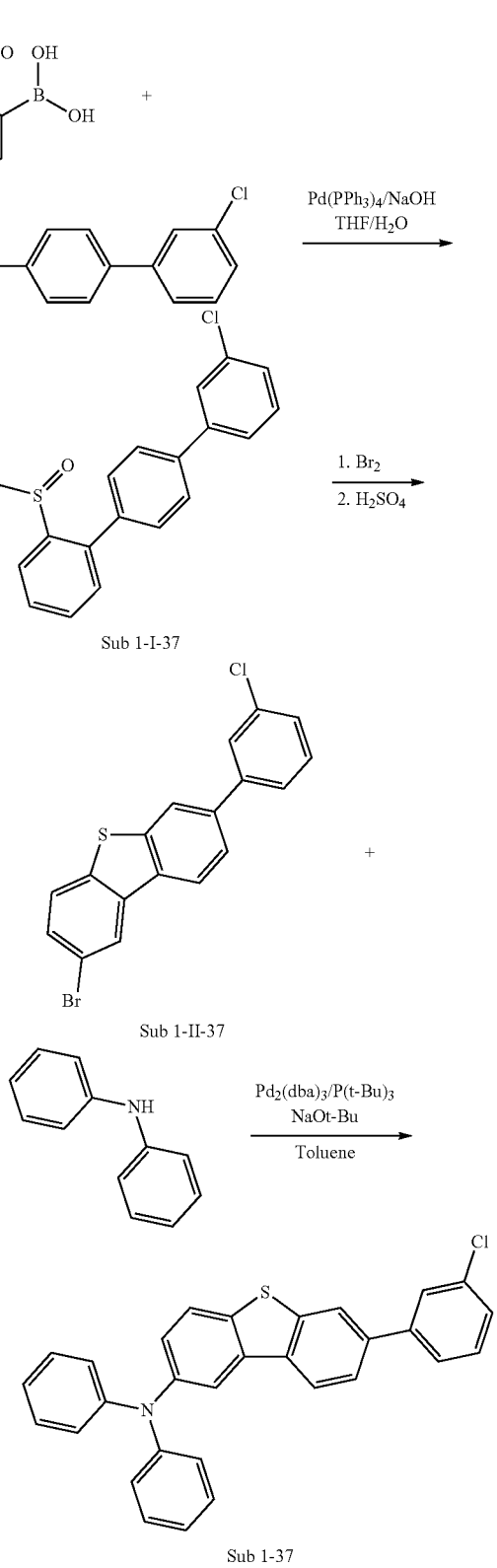

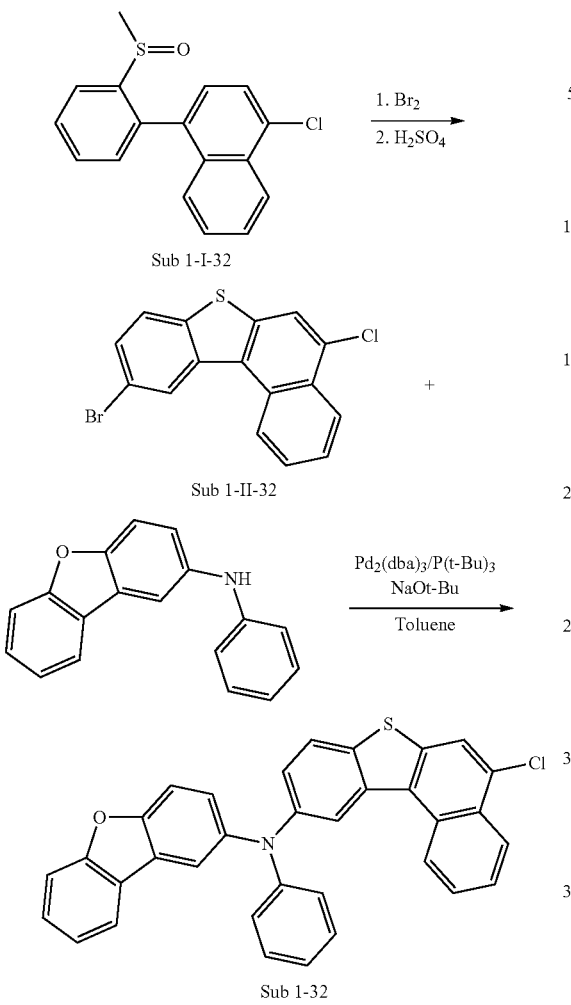

(1) Synthesis of Sub 1I-32

(2-(Methylsulfinyl)phenyl)boronic acid (30 g, 0.163 mol), 1-bromo-4-chloronaphthalene (39.37 g, 0.163 mol), Pd(PPh$_3$)$_4$ (5.66 g, 0.0049 mol), NaOH (19.6 g, 0.489 mol) were added in THF(550 mL) and H20(130 mL), and the same procedure as described in the synthesis method of Sub 1-1 above was carried out to obtain 40 g of Sub 1-I-32(yield: 82%).

(2) Synthesis of Sub 1-II-32

After Sub1-I-32 (40 g, 0.133 mol), Br$_2$ (17 mL, 0.399 mol) were stirred for 5 hours and washed with water, followed by adding sulfuric acid(250 mL) to the Intermediate and by stirring for 6 hours. The product was recrystallized again by toluene so as to obtain 40g of Sub 1-II-32 (yield: 87%).

(3) Synthesis of Sub 1-32

Sub1-II-32 (40 g, 0.115 mol), N-phenyldibenzo[b,d]furan-2-amine (30 g, 0.115 mol), Pd$_2$(dba)$_3$ (3.2 g, 0.00345 mol), (t-Bu)$_3$P (2.83 mL, 0.0069 mol), NaOt-Bu (33.1 g, 0.345 mol) were added in anhydrous Toluene(380 mL) and the same procedure as described in the synthesis method of Sub 1-1 above was carried out to obtain 33 g of Sub 1-32 (yield: 55%).

(1) Synthesis of Sub 1-I-37

(2-(Methylsulfinyl)phenyl)boronic acid (60 g, 0.326 mol), 4'-bromo-3-chloro-1,1'-biphenyl (87.22 g, 0.326 mol), Pd(PPh$_3$)$_4$ (11.3 g, 0.00978 mol), NaOH (39.5 g, 0.978 mol) were added in THF(1000 mL) and H$_2$O(300 mL), and the same procedure as described in the synthesis method of Sub 1-1 above was carried out to obtain 72 g of Sub 1-I-37(yield: 68%).

(2) Synthesis of Sub 1-II-37

After Sub1-I-37 (50 g, 0.153 mol), Br2 (24 mL, 0.459 mol) were stirred for 5 hours and washed with water, followed by adding sulfuric acid(400 mL) to the Intermediate and by stirring for 6 hours. The product was recrystallized again by toluene so as to obtain 27.5 g of Sub 1-II-37 (yield: 48%).

(3) Synthesis of Sub 1-37

Sub1-II-37 (20 g, 0.0535 mol), diphenylamine (9 g, 0.0535 mol), Pd$_2$(dba)$_3$ (1.47 g, 0.00161 mol), (t-Bu)$_3$P (1.3 mL, 0.0032 mol), NaOt-Bu (15.5 g, 0.161 mol) were added in anhydrous Toluene(200 mL) and the same procedure as described in the synthesis method of Sub 1-1 above was carried out to obtain 22 g of Sub 1-37 (yield: 89%).

Meanwhile, examples of Sub 1 compounds include, but are not limited to, the following compounds, and FD-MS values of the compounds are given in Table 1 below.

Sub1-1

Sub1-2

Sub1-3

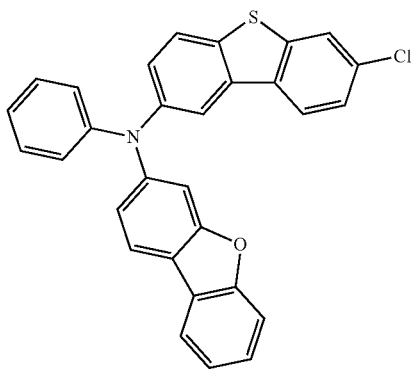

Sub1-4

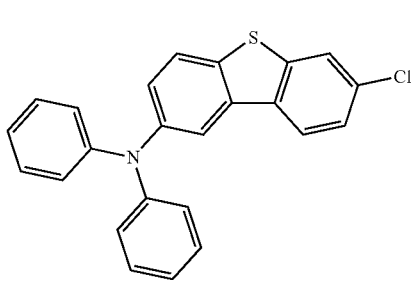

Sub1-5

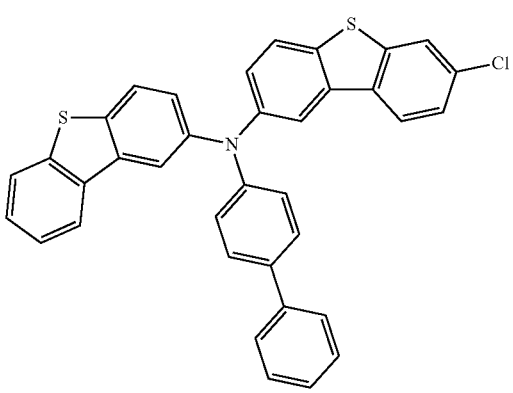

Sub1-6

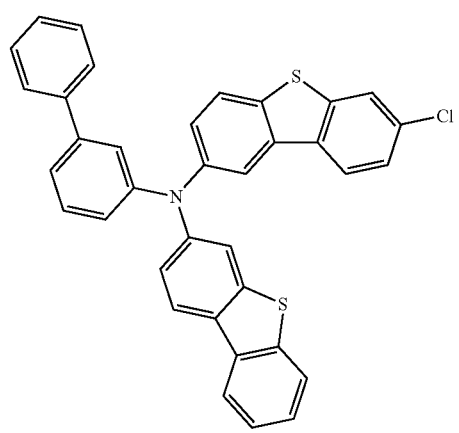

Sub1-7

Sub1-8
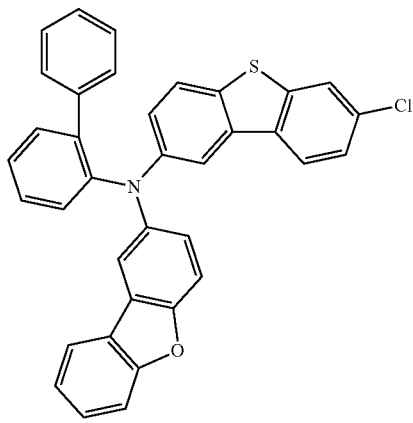
Sub1-12
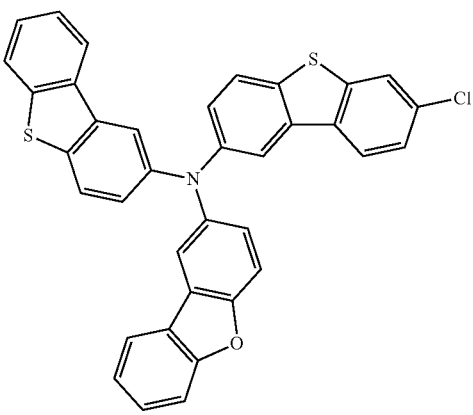
Sub1-9
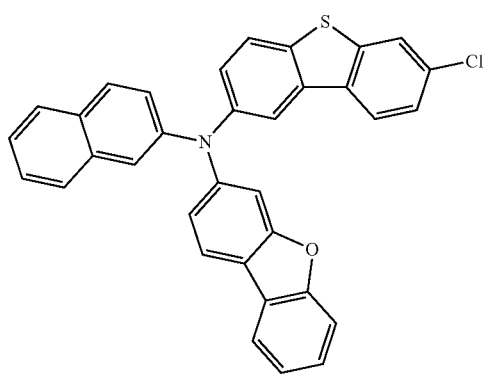
Sub1-13
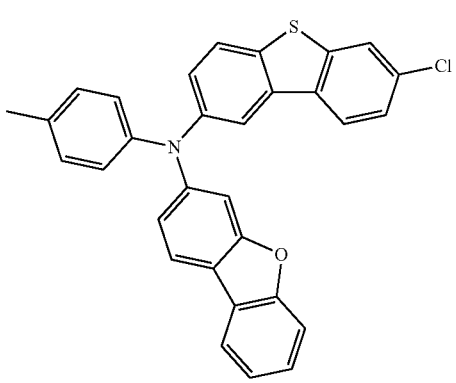
Sub1-10
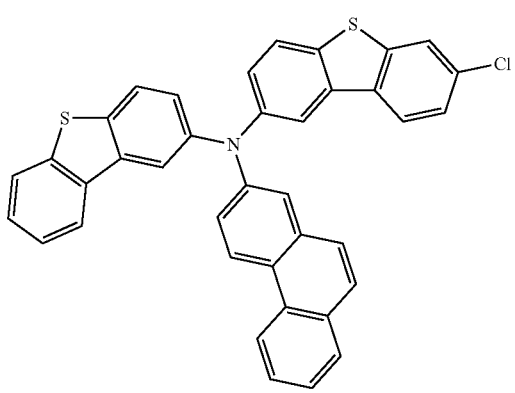
Sub1-14
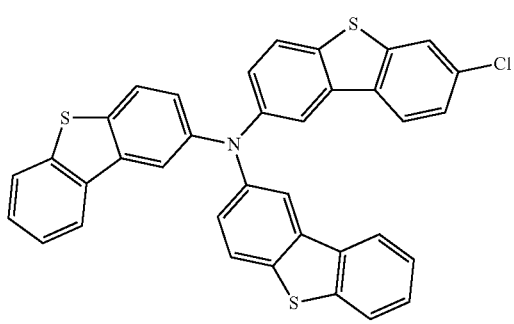
Sub1-11
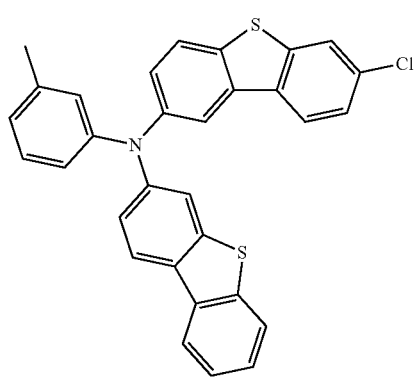
Sub1-15
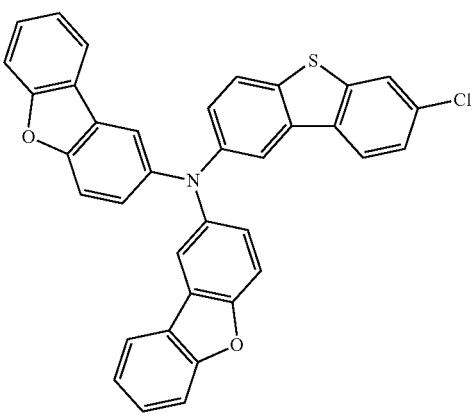

Sub1-16
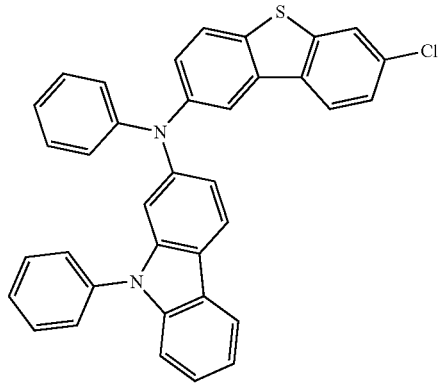
Sub1-17
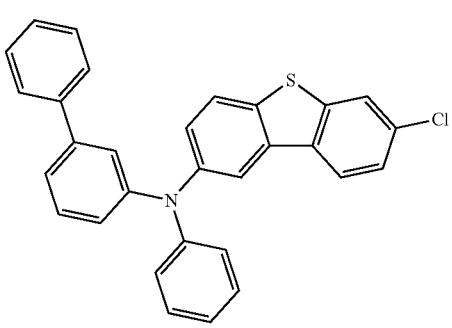
Sub1-18
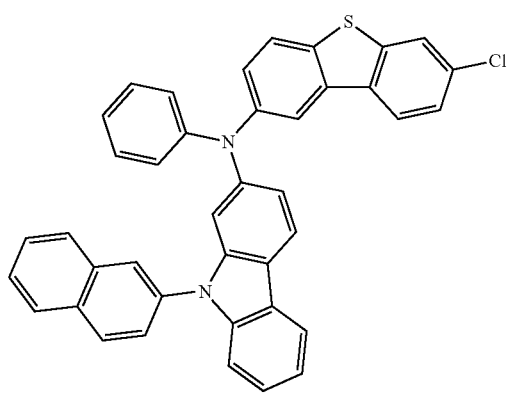
Sub1-19
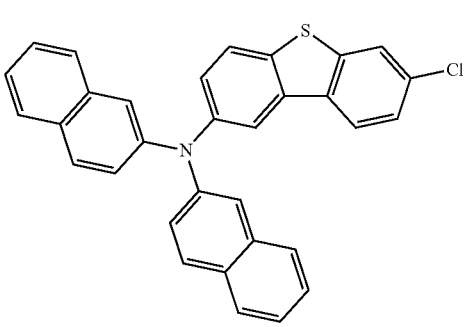
Sub1-20
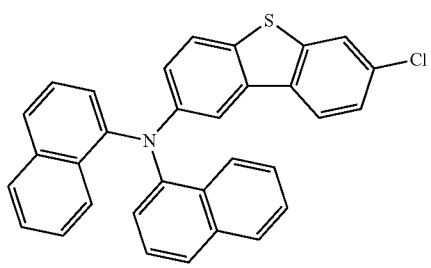
Sub1-21
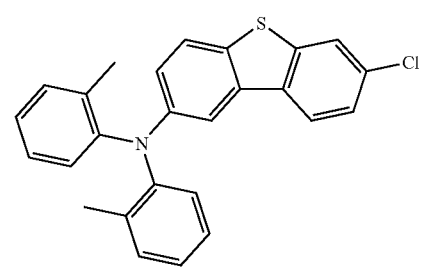
Sub1-22
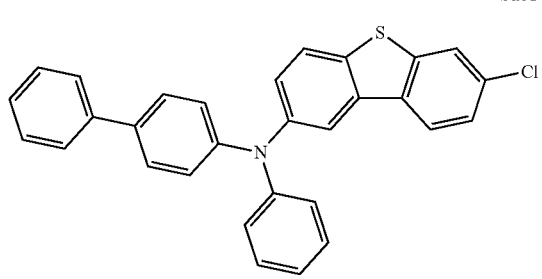
Sub1-23
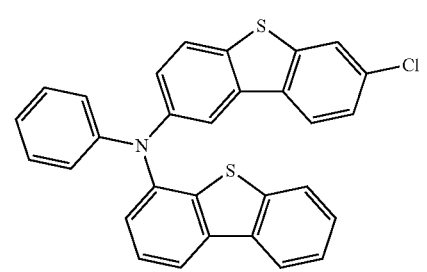
Sub1-24
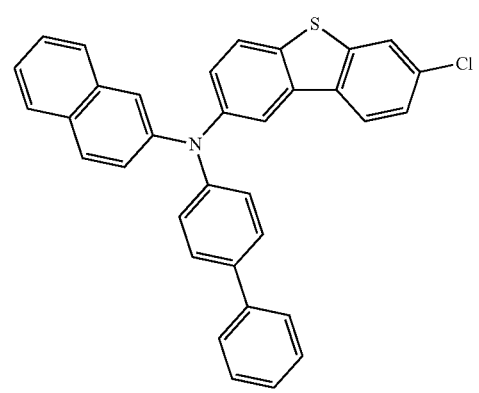

-continued
Sub1-25
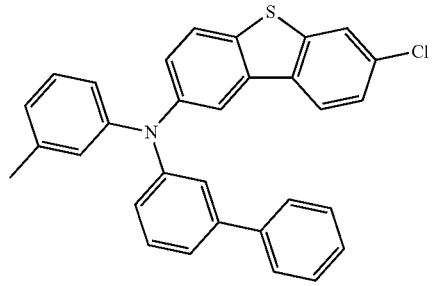
Sub1-26
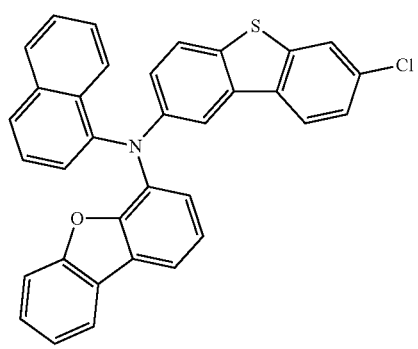
Sub1-27
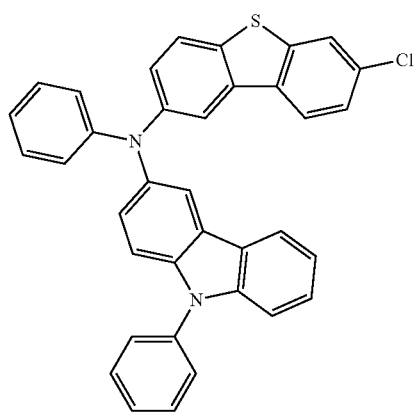
Sub1-18
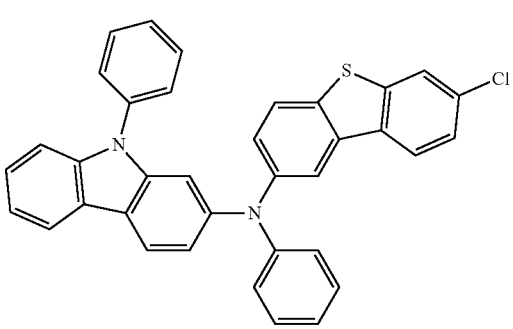
Sub1-29
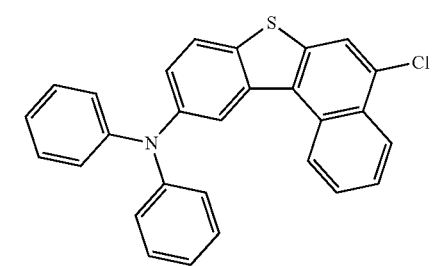
Sub1-30
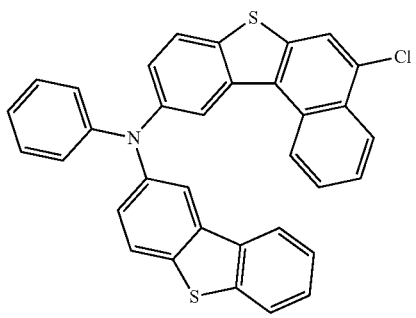
Sub1-31
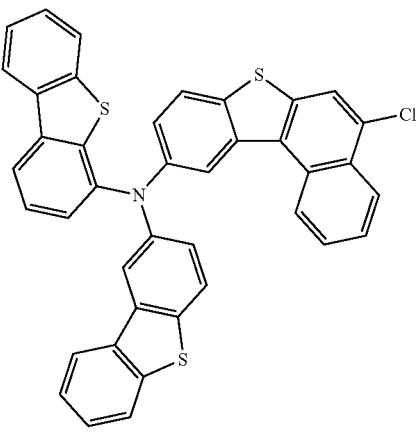
Sub1-32
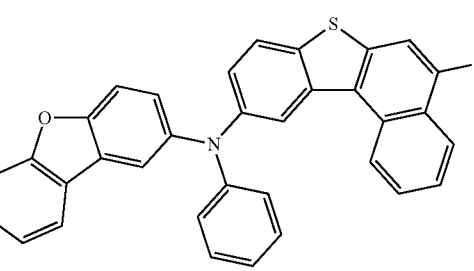
Sub1-33
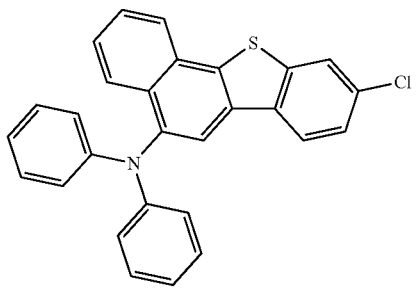

-continued
Sub1-34
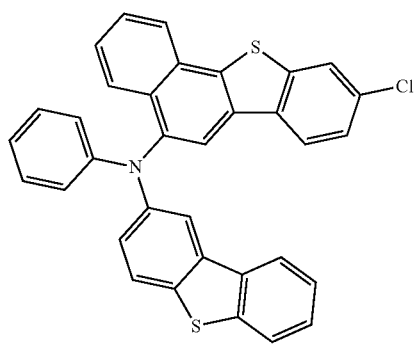
Sub1-35
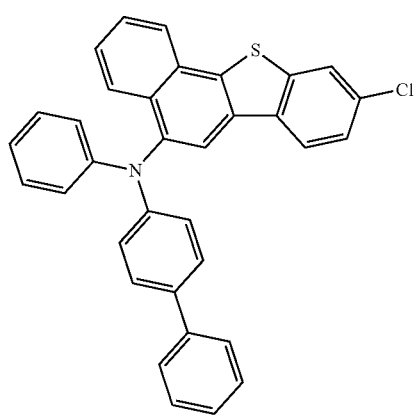
Sub1-36
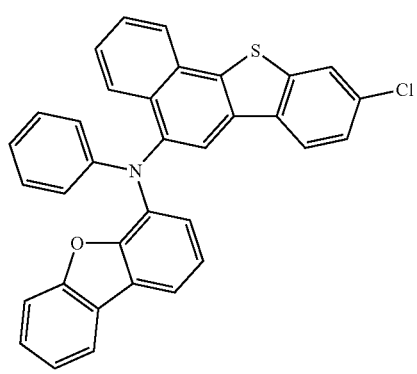
Sub1-37
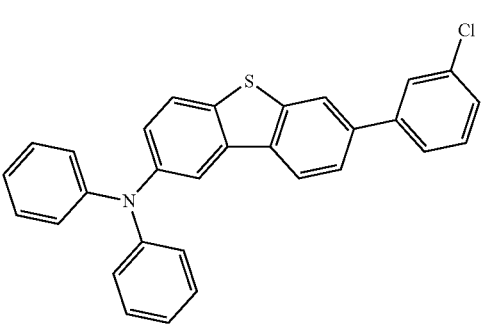
Sub1-38
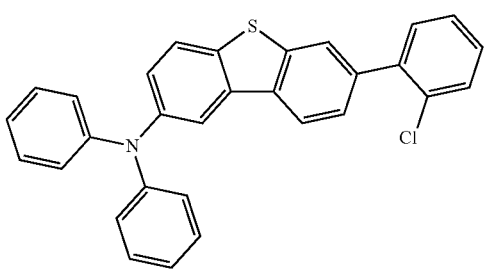
Sub1-39
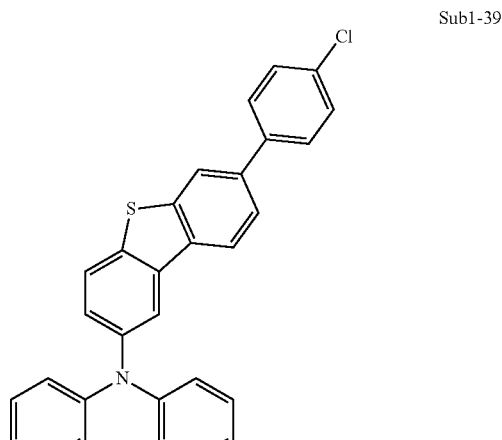
Sub1-40
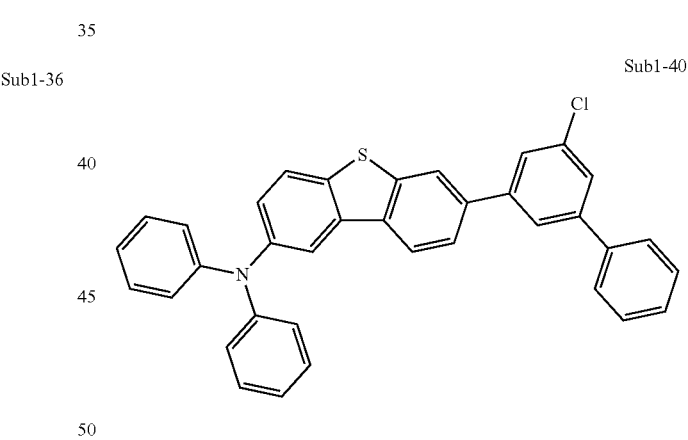
Sub1-41
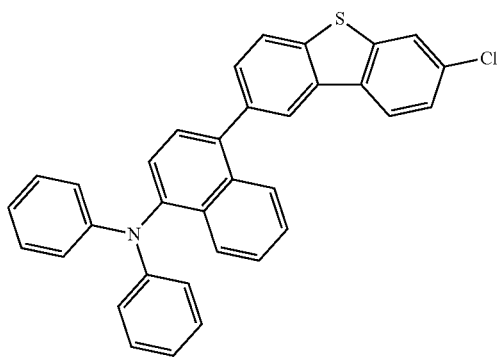

Sub1-42

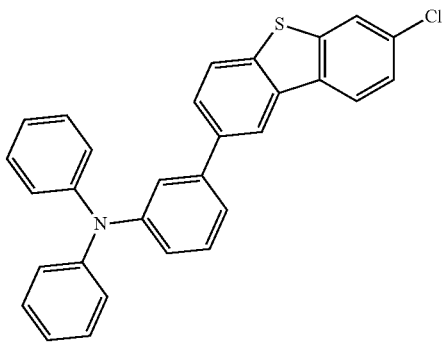

Sub1-43

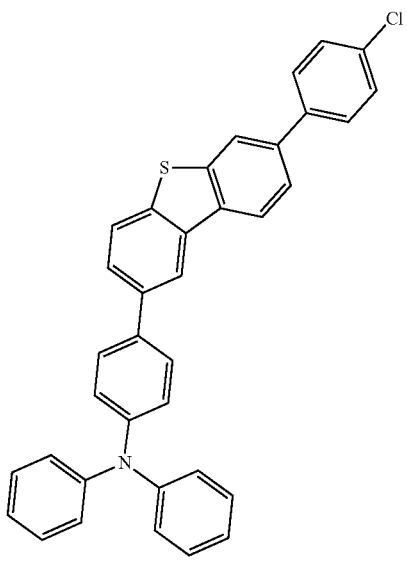

Synthesis Examples of Sub 2

Sub 2 of Reaction Scheme 1 can be synthesized, but not limited to, the followings.

1. Synthesis Examples of Sub 2-1

<Reaction Scheme 7>

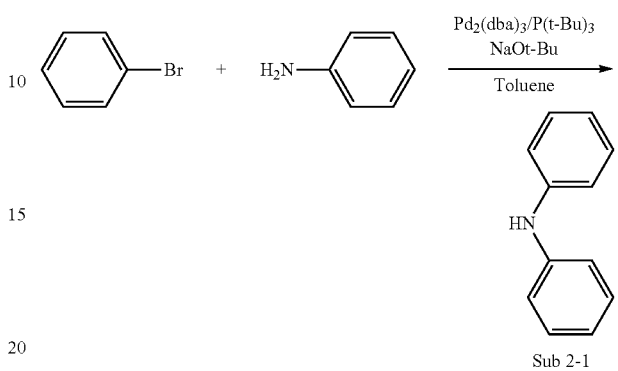

Sub 2-1

The starting material bromobenzene (40.68 g, 259.09 mmol) was dissolved in Toluene in a round bottom flask, and aniline (26.54 g, 285.00 mmol), Pd$_2$(dba)$_3$ (7.12 g, 7.77 mmol), 50% P(t-Bu)$_3$ (10.1 ml, 20.73 mmol), NaOt-Bu (74.70 g, 777.28 mmol) were added to the reaction solution, followed by stirring at 80° C. Upon completion of the reaction, the reaction product was extracted with CH$_2$Cl$_2$ and water. The organic material layer was dried with MgSO$_4$ and concentrated, and then the product was separated by a silicagel column and recrystallized to obtain 32.88 g of product Sub 2-1(yield: 75%).

2. Synthesis Examples of Sub 2-2

<Reaction Scheme 8>

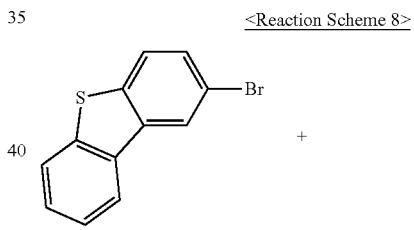

+

TABLE 1

| compound | FD-MS | compound | FD-MS |
|---|---|---|---|
| Sub 1-1 | m/z = 491.06(C$_{30}$H$_{18}$ClNS$_2$ = 492.05) | Sub 1-2 | m/z = 491.06(C$_{30}$H$_{18}$ClNS$_2$ = 492.05) |
| Sub 1-3 | m/z = 475.08(C$_{30}$H$_{18}$ClNSO = 475.99) | Sub 1-4 | m/z = 475.08(C$_{30}$H$_{18}$ClNSO = 475.99) |
| Sub 1-5 | m/z = 385.07(C$_{24}$H$_{16}$ClNS = 385.91) | Sub 1-6 | m/z = 567.09(C$_{36}$H$_{22}$ClNS$_2$ = 568.15) |
| Sub 1-7 | m/z = 567.09(C$_{36}$H$_{22}$ClNS$_2$ = 568.15) | Sub 1-8 | m/z = 551.11(C$_{36}$H$_{22}$ClNOS = 552.09) |
| Sub 1-9 | m/z = 525.10(C$_{34}$H$_{20}$ClNOS = 526.05) | Sub 1-10 | m/z = 591.09(C$_{38}$H$_{22}$ClNS$_2$ = 592.17) |
| Sub 1-11 | m/z = 505.07(C$_{31}$H$_{20}$ClNS$_2$ = 506.08) | Sub 1-12 | m/z = 581.07(C$_{36}$H$_{20}$ClNOS$_2$ = 582.13) |
| Sub 1-13 | m/z = 489.10(C$_{31}$H$_{20}$ClNOS = 490.02) | Sub 1-14 | m/z = 597.04(C$_{36}$H$_{20}$ClNS$_3$ = 598.19) |
| Sub 1-15 | m/z = 565.09(C$_{36}$H$_{20}$ClNO$_2$S = 566.07) | Sub 1-16 | m/z = 550.13(C$_{36}$H$_{23}$ClN$_2$S = 551.10) |
| Sub 1-17 | m/z = 461.10(C$_{30}$H$_{20}$ClNS = 462.01) | Sub 1-18 | m/z = 600.14(C$_{40}$H$_{25}$ClN$_2$S = 601.16) |
| Sub 1-19 | m/z = 485.10(C$_{32}$H$_{20}$ClNS = 486.03) | Sub 1-20 | m/z = 485.10(C$_{32}$H$_{20}$ClNS = 486.03) |
| Sub 1-21 | m/z = 413.10(C$_{26}$H$_{20}$ClNS = 413.96) | Sub 1-22 | m/z = 461.10(C$_{30}$H$_{20}$ClNS = 462.01) |
| Sub 1-23 | m/z = 491.06(C$_{30}$H$_{18}$ClNS$_2$ = 492.05) | Sub 1-24 | m/z = 511.12(C$_{34}$H$_{22}$ClNS = 512.07) |
| Sub 1-25 | m/z = 475.12(C$_{31}$H$_{22}$ClNS = 476.03) | Sub 1-26 | m/z = 525.10(C$_{34}$H$_{20}$ClNOS = 526.05) |
| Sub 1-27 | m/z = 550.13(C$_{36}$H$_{23}$ClN$_2$S = 551.10) | Sub 1-28 | m/z = 550.13(C$_{36}$H$_{23}$ClN$_2$S = 551.10) |
| Sub 1-29 | m/z = 435.08(C$_{28}$H$_{18}$ClNS = 435.97) | Sub 1-30 | m/z = 541.07(C$_{34}$H$_{20}$ClNS$_2$ = 542.11) |
| Sub 1-31 | m/z = 647.06(C$_{40}$H$_{22}$ClNS$_3$ = 648.25) | Sub 1-32 | m/z = 525.10(C$_{34}$H$_{20}$ClNOS = 526.05) |
| Sub 1-33 | m/z = 435.08(C$_{28}$H$_{18}$ClNS = 435.97) | Sub 1-34 | m/z = 541.07(C$_{34}$H$_{20}$ClNS$_2$ = 542.11) |
| Sub 1-35 | m/z = 511.12(C$_{34}$H$_{22}$ClNS = 512.07) | Sub 1-36 | m/z = 525.10(C$_{34}$H$_{20}$ClNOS = 526.05) |
| Sub 1-37 | m/z = 461.10(C$_{30}$H$_{20}$ClNS = 462.01) | Sub 1-38 | m/z = 461.10(C$_{30}$H$_{20}$ClNS = 462.01) |
| Sub 1-39 | m/z = 461.10(C$_{30}$H$_{20}$ClNS = 462.01) | Sub 1-40 | m/z = 537.13(C$_{36}$H$_{24}$ClNS = 538.11) |
| Sub 1-41 | m/z = 511.12(C$_{34}$H$_{22}$ClNS = 512.07) | Sub 1-42 | m/z = 461.10(C$_{30}$H$_{20}$ClNS = 462.01) |
| Sub 1-43 | m/z = 537.13(C$_{36}$H$_{24}$ClNS = 538.11) | | |

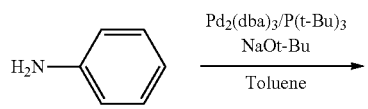

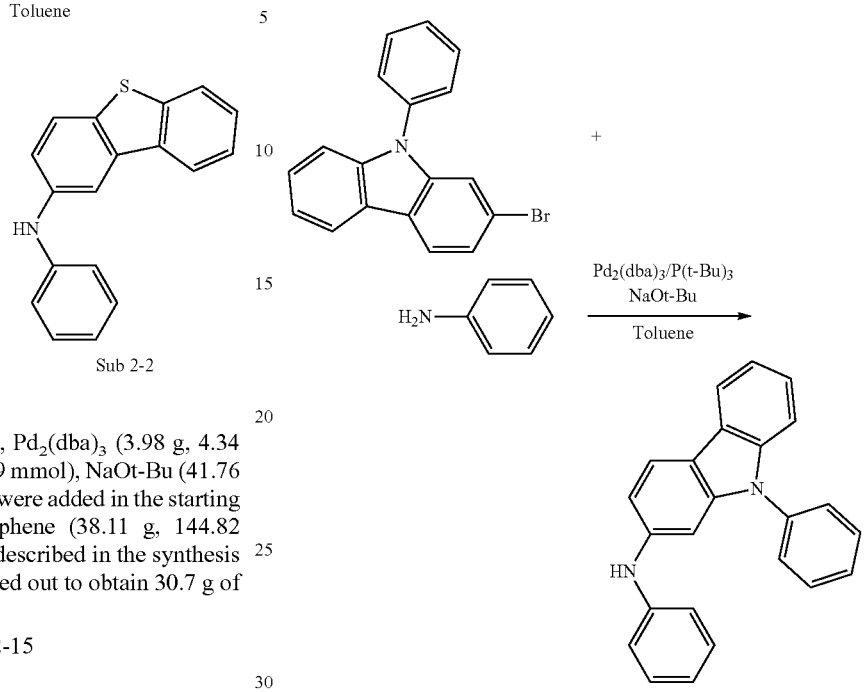

4. Synthesis Examples of Sub 2-20

<Reaction Scheme 10>

Aniline (14.84 g, 159.30 mmol), Pd₂(dba)₃ (3.98 g, 4.34 mmol), 50% P(t-Bu)₃ (5.6 ml, 11.59 mmol), NaOt-Bu (41.76 g, 434.47 mmol), toluene (760 ml) were added in the starting material 2-bromodibenzo[b,d]thiophene (38.11 g, 144.82 mmol) and the same procedure as described in the synthesis method of Sub 2-1 above was carried out to obtain 30.7 g of Sub 2-2 (yield: 77%).

3. Synthesis Examples of Sub 2-15

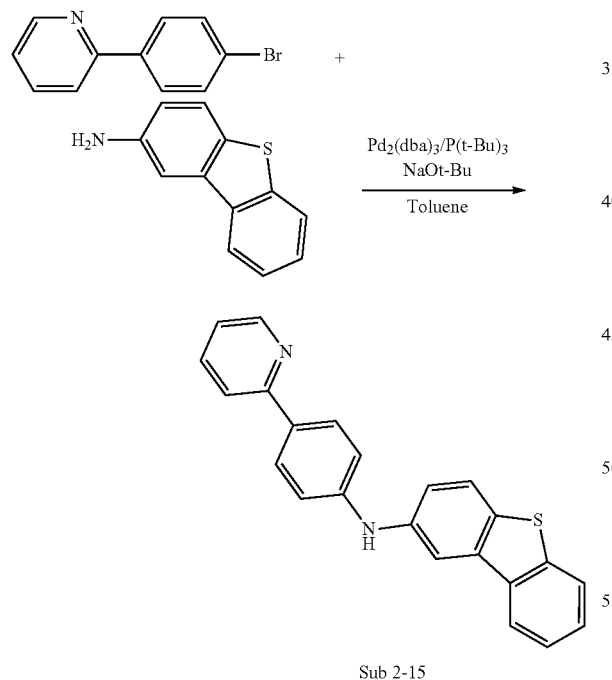

Dibenzo[b,d]thiophen-2-amine (9.9 g, 49.48 mmol), Pd₂(dba)₃ (1.24 g, 1.35 mmol), 50% P(t-Bu)₃ (1.8 ml, 3.60 mmol), NaOt-Bu (12.97 g, 134.95 mmol), toluene (315 ml) were added in the starting material 2-(4-bromophenyl)pyridine (10.53 g, 44.98 mmol) and the same procedure as described in the synthesis method of Sub 2-1 above was carried out to obtain 8.32 g of Sub 2-15 (yield: 53%).

Aniline (4.68 g, 50.22 mmol), Pd₂(dba)₃ (1.25 g, 1.37 mmol), 50% P(t-Bu)₃ (1.8 ml, 3.65 mmol), NaOt-Bu (13.16 g, 136.96 mmol), toluene (320 ml) were added in the starting material 2-bromo-9-phenyl-9H-carbazole (14.71 g, 45.65 mmol) and the same procedure as described in the synthesis method of Sub 2-1 above was carried out to obtain 10.99 g of Sub 2-20 (yield: 72%).

5. Synthesis Examples of Sub 2-30

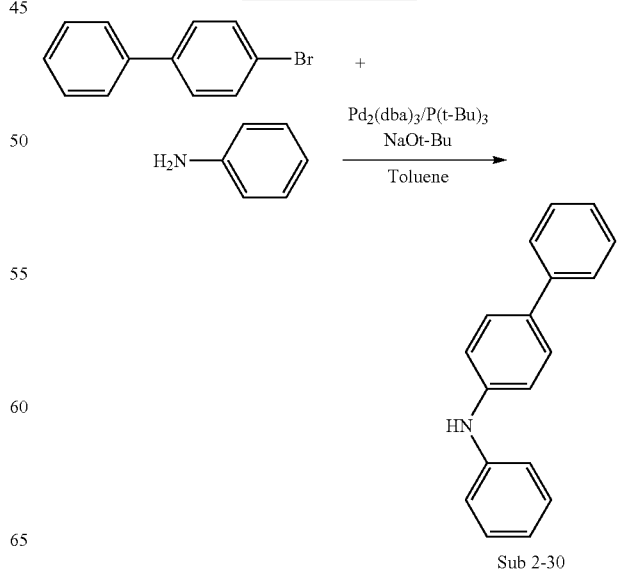

Aniline (10.39 g, 111.60 mmol), Pd$_2$(dba)$_3$ (2.79 g, 3.04 mmol), 50% P(t-Bu)$_3$ (4.0 ml, 8.12 mmol), NaOt-Bu (29.25 g, 304.38 mmol), toluene (710 ml) were added in the starting material 4-bromo-1,1'-biphenyl (23.65 g, 101.46 mmol) and the same procedure as described in the synthesis method of Sub 2-1 above was carried out to obtain 20.66 g of Sub 2-30 (yield: 83%).
Sub2-1
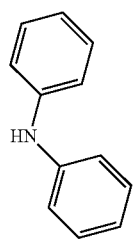
Sub2-2
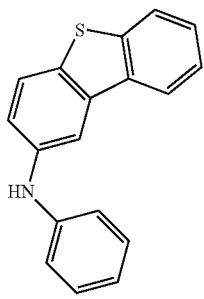
Sub2-3
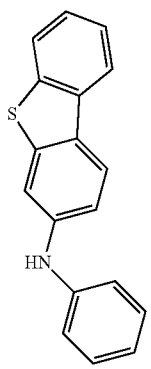
Sub2-4
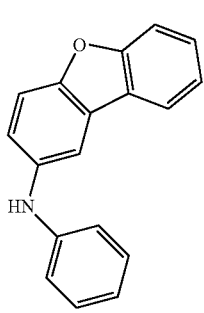
-continued
Sub2-5
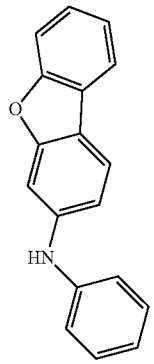
Sub2-6
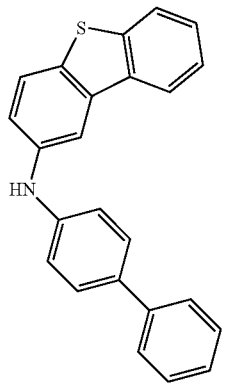
Sub2-7
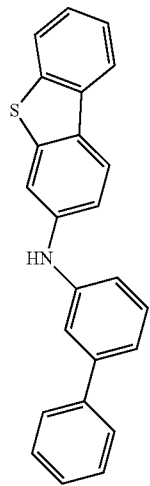
Sub2-8
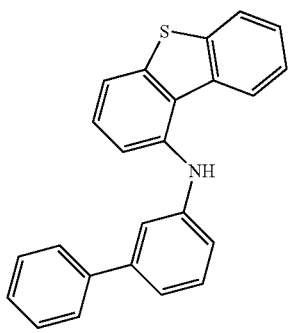

Sub2-9
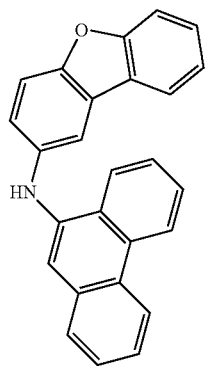
Sub2-10
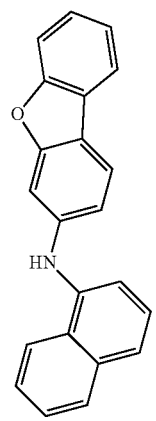
Sub2-11
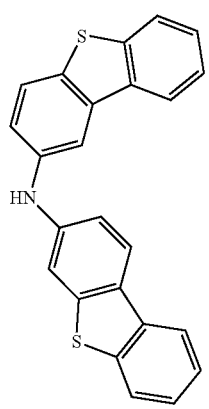
Sub2-12
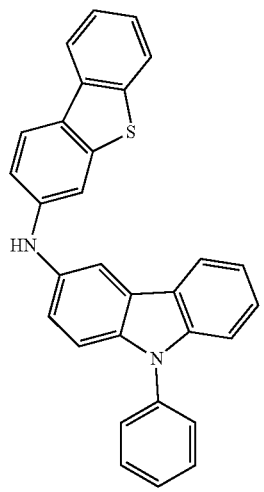
Sub2-13
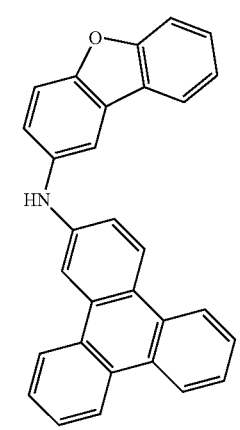
Sub2-14
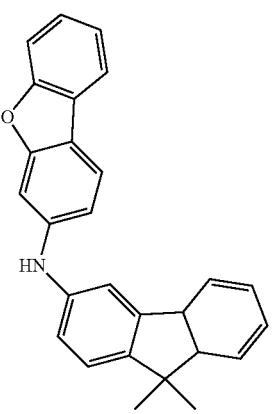

Sub2-15
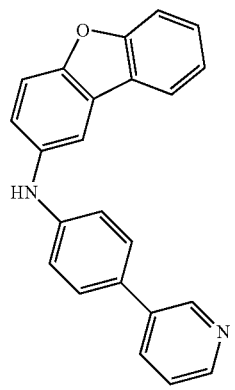
Sub2-16
Sub2-17
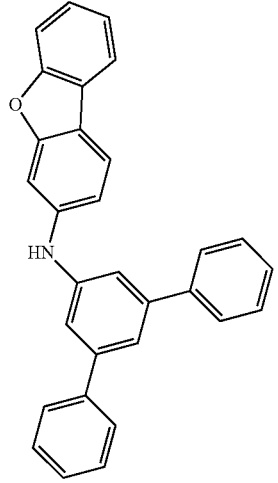
Sub2-18
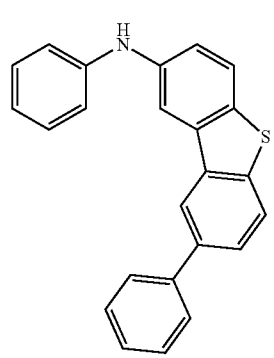
Sub2-19
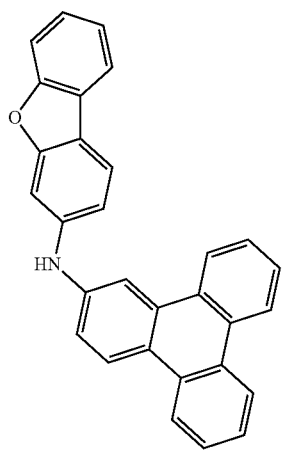
Sub2-20
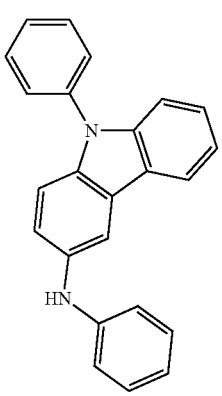
Sub2-21
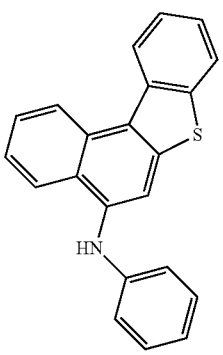
Sub2-22
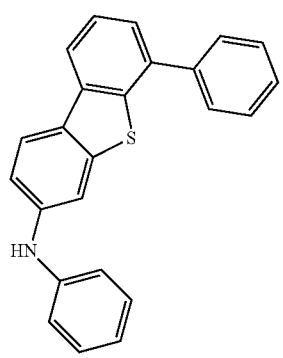

Sub2-23
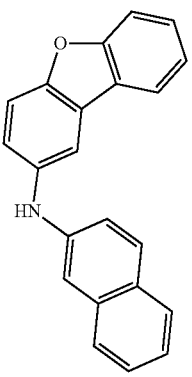
Sub2-24
Sub2-25
Sub2-26
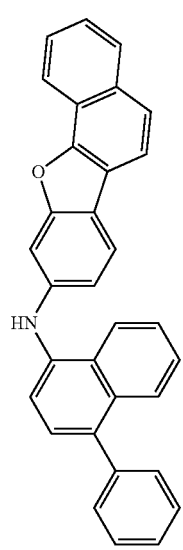
Sub2-27
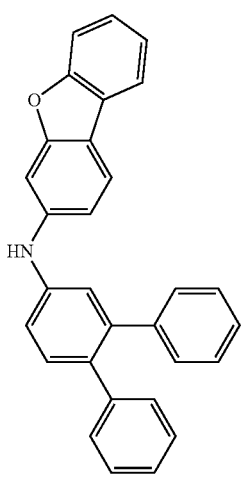
Sub2-28
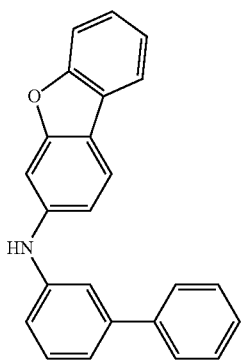

-continued

Sub2-29

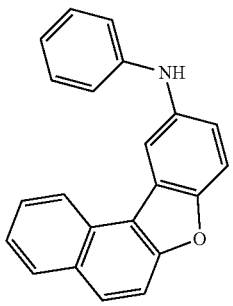

-continued

Sub2-30

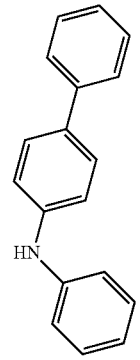

TABLE 2

| compound | FD-MS | compound | FD-MS |
|---|---|---|---|
| Sub 2-1 | m/z = 169.09($C_{12}H_{11}N$ = 169.22) | Sub 2-2 | m/z = 275.08($C_{18}H_{13}NS$ = 275.37) |
| Sub 2-3 | m/z = 275.08($C_{18}H_{13}NS$ = 275.37) | Sub 2-4 | m/z = 259.10($C_{18}H_{13}NO$ = 259.31) |
| Sub 2-5 | m/z = 259.10($C_{18}H_{13}NO$ = 259.31) | Sub 2-6 | m/z = 351.11($C_{24}H_{17}NS$ = 351.47) |
| Sub 2-7 | m/z = 351.11($C_{24}H_{17}NS$ = 351.47) | Sub 2-8 | m/z = 351.11($C_{24}H_{17}NS$ = 351.47) |
| Sub 2-9 | m/z = 359.13($C_{26}H_{17}NO$ = 359.43) | Sub 2-10 | m/z = 309.12($C_{22}H_{15}NO$ = 309.37) |
| Sub 2-11 | m/z = 309.12($C_{22}H_{15}NO$ = 309.37) | Sub 2-12 | m/z = 440.13($C_{30}H_{20}N_2S$ = 440.56) |
| Sub 2-13 | m/z = 409.15($C_{30}H_{19}NO$ = 409.49) | Sub 2-14 | m/z = 375.16($C_{27}H_{21}NO$ = 375.47) |
| Sub 2-15 | m/z = 352.10($C_{23}H_{16}N_2S$ = 352.46) | Sub 2-16 | m/z = 335.13($C_{24}H_{27}NO$ = 335.41) |
| Sub 2-17 | m/z = 411.16($C_{30}H_{21}NO$ = 411.50) | Sub 2-18 | m/z = 351.11($C_{24}H_{17}NS$ = 351.47) |
| Sub 2-19 | m/z = 409.15($C_{30}H_{19}NO$ = 409.49) | Sub 2-20 | m/z = 334.1($C_{24}H_{18}N_2$ = 334.41) |
| Sub 2-21 | m/z = 325.09($C_{22}H_{15}NS$ = 325.43) | Sub 2-22 | m/z = 351.11($C_{24}H_{17}NS$ = 351.47) |
| Sub 2-23 | m/z = 309.12($C_{22}H_{15}NO$ = 309.37) | Sub 2-24 | m/z = 410.18($C_{30}H_{22}N_2$ = 410.52) |
| Sub 2-25 | m/z = 349.11($C_{24}H_{15}NO_2$ = 349.39) | Sub 2-26 | m/z = 435.16($C_{32}H_{21}NO$ = 435.53) |
| Sub 2-27 | m/z = 411.16($C_{30}H_{21}NO$ = 411.50) | Sub 2-28 | m/z = 335.13($C_{24}H_{27}NO$ = 335.41) |
| Sub 2-29 | m/z = 309.12($C_{22}H_{15}NO$ = 309.37) | Sub 2-30 | m/z = 245.12($C_{18}H_{15}N$ = 245.32) |

Synthesis Examples of Final Products

1. Synthesis Examples of P-1

<Reaction Scheme 12>

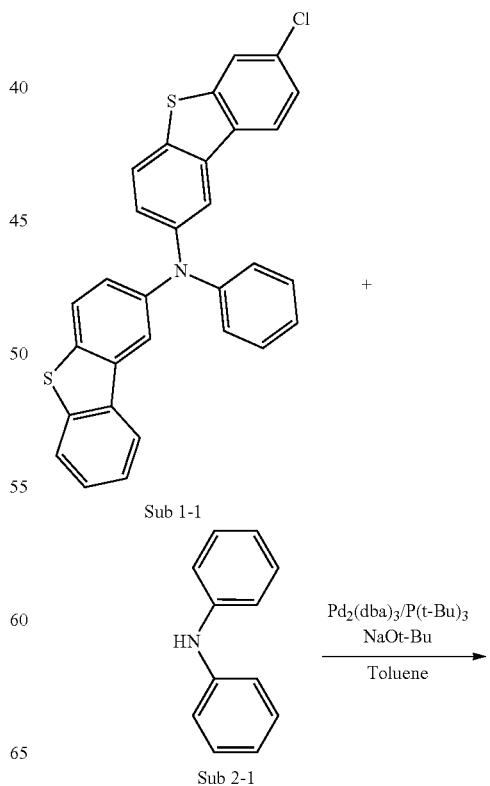

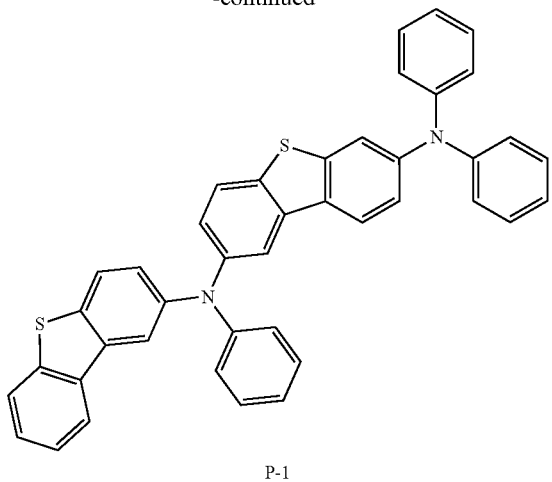

P-1

The obtained material Sub 1-1 (7.8 g, 15.94 mmol) was dissolved in Toluene (150 mL) in a round bottom flask, and Sub 2-1 (2.7 g, 15.94 mmol), $Pd_2(dba)_3$ (0.44 g, 0.47 mmol), 50% $P(t\text{-}Bu)_3$ (1.95 ml, 0.97 mmol), NaOt-Bu (4.6 g, 47.84 mmol) were added to the reaction solution, followed by stirring at 130° C. Upon completion of the reaction, the reaction product was extracted with $CH_2Cl_2$ and water. The organic material layer was dried with $MgSO_4$ and concentrated, and then the product was separated by a silicagel column and recrystallized to obtain 8.1 g of product P-1 (yield: 80%).

2. Synthesis Examples of P-13

<Reaction Scheme 13>

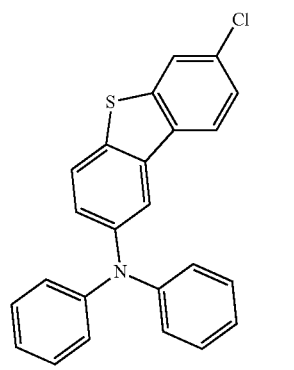

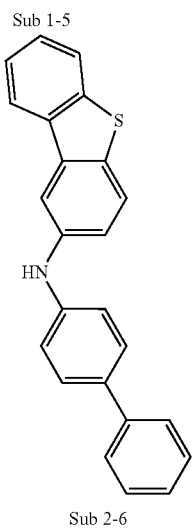

Sub 2-6

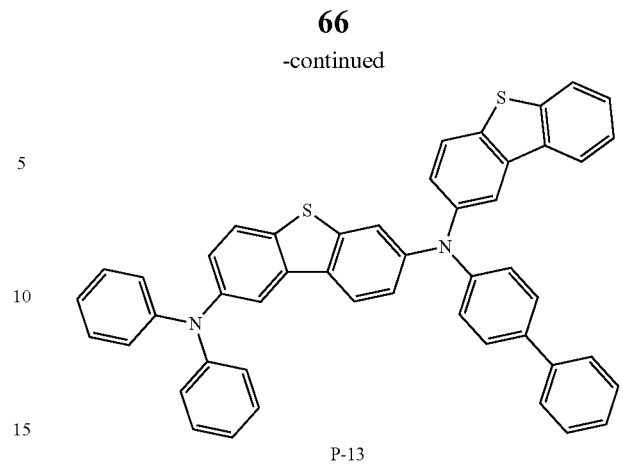

P-13

Using the obtained materials Sub 1-5 (10 g, 25.91 mmol), Sub 2-6 (9.1 g, 25.91 mmol), $Pd_2(dba)_3$ (0.72 g, 0.0077 mmol), $P(t\text{-}Bu)_3$ (0.6 mL, 0.016 mmol), NaOt-Bu (7.5 g, 77.7 mmol), the same procedure as described in the synthesis method of P-1 was carried out to obtain 11 g of P-3(yield: 61%).

3. Synthesis Examples of P-22

<Reaction Scheme 14>

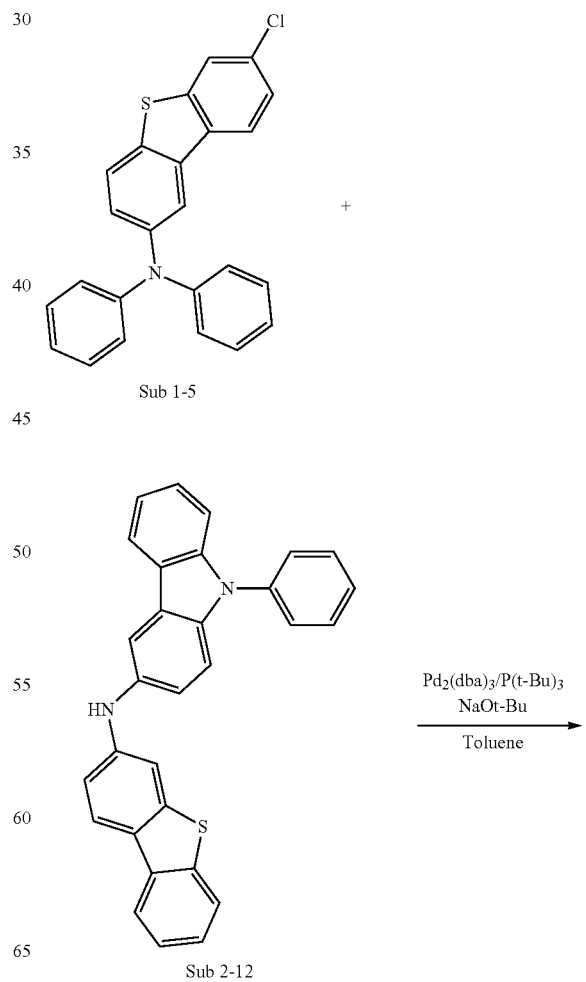

Sub 2-12

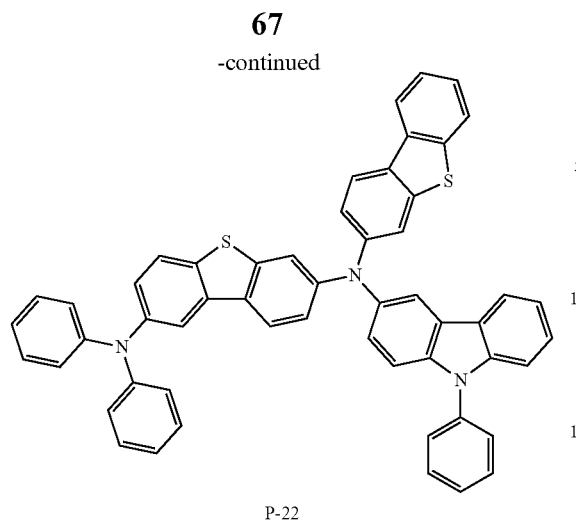

P-22

Using the obtained materials Sub 1-5 (10 g, 25.91 mmol), Sub 2-12 (11.4 g, 25.91 mmol), Pd$_2$(dba)$_3$ (0.72 g, 0.0077 mmol), P(t-Bu)$_3$ (0.6 mL, 0.016 mmol), NaOt-Bu (7.5 g, 77.7 mmol), the same procedure as described in the synthesis method of P-1 was carried out to obtain 15 g of P-22(yield: 73%).

4. Synthesis Examples of P-59

<Reaction Scheme 15>

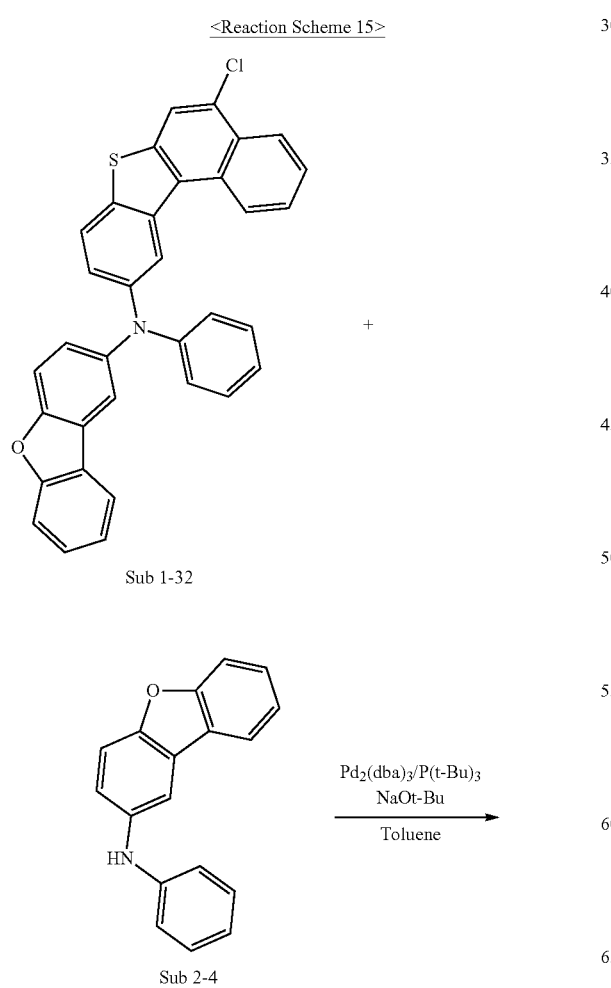

Sub 1-32

Sub 2-4

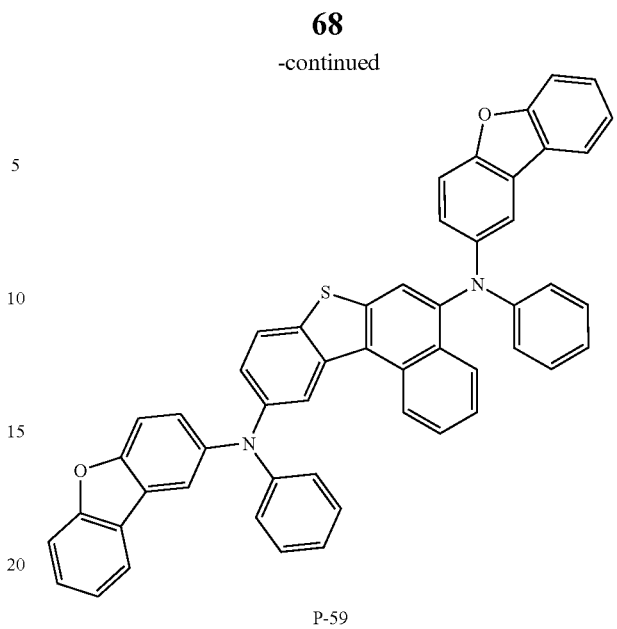

P-59

Using the obtained materials Sub 1-32 (15 g, 0.0285 mol), Sub 2-4 (7.4 g, 0.0285 mmol), Pd$_2$(dba)$_3$ (0.78 g, 0.9 mmol), P(t-Bu)$_3$ (0.8 mL, 0.18 mmol), NaOt-Bu (8.2 g, 0.0855 mol), the same procedure as described in the synthesis method of P-1 was carried out to obtain 19 g of P-59(yield: 89%).

5. Synthesis Examples of P-72

<Reaction Scheme 16>

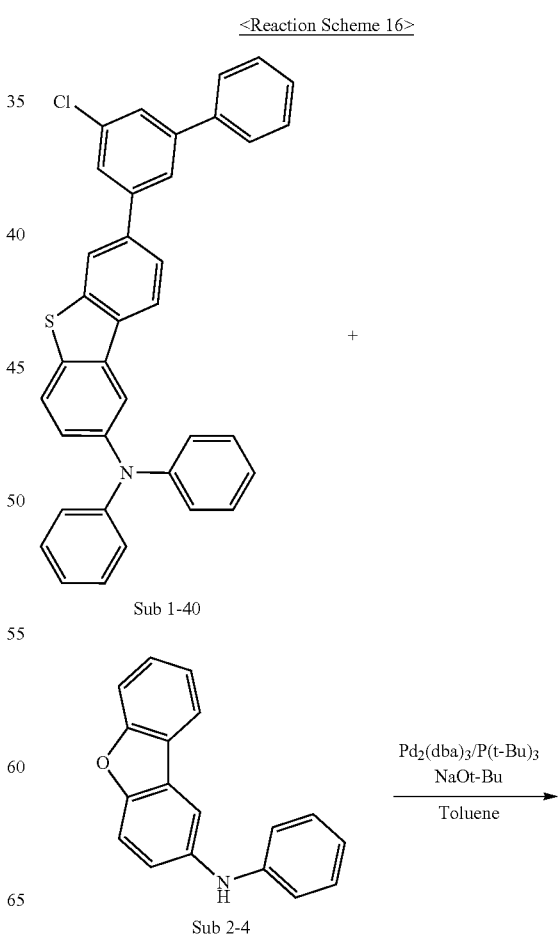

Sub 1-40

Sub 2-4

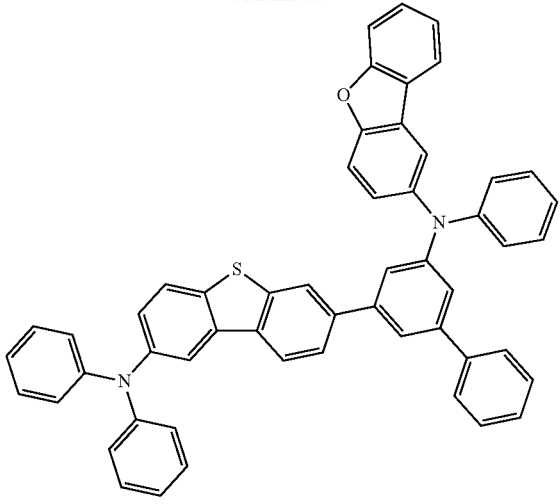

P-72

Using the obtained materials Sub 1-40 (12 g, 0.0223 mol), Sub 2-4 (5.8 g, 0.0223 mmol), $Pd_2(dba)_3$ (0.70 g, 0.9 mmol), $P(t-Bu)_3$ (0.67 mL, 0.16 mmol), NaOt-Bu (6.5 g, 0.067 mol), the same procedure as described in the synthesis method of P-1 was carried out to obtain 13 g of P-72(yield: 76%).

Meanwhile, FD-MS values for the inventive compounds P-1 to P-76 prepared according to the Synthesis examples above are given in Table 3 below.

Manufacture and Evaluation of Organic Electric Element

EXAMPLE 1

Manufacture and Test of Red OLED

First, on an ITO layer (anode) formed on a glass substrate, $N^1$-(naphthalen-2-yl)-$N^4$,$N^4$-bis(4-(naphthalen-2-yl(phenyl)amino)phenyl)-$N^1$-phenylbenzene-1,4-diamine(hereinafter will be abbreviated as 2-TNATA) was vacuum-deposited to form a hole injection layer with a thickness of 60 nm, and N,N'-bis(1-naphthalenyl)-N,N'-bis-phenyl-(1,1'-biphenyl)-4,4'-diamine (hereinafter will be abbreviated as NPB) was vacuum-deposited to form a hole transport layer with a thickness of 60 nm. Then, the compound of the present invention represented by Formula (1) was vacuum deposited to form an emitting-auxiliary layer with a thickness of 20 nm. On the emitting-auxiliary layer, an emitting layer with a thickness of 30 nm was deposited using CBP[4,4'-N,N-dicarbazole-biphenyl] as a host doped with $(piq)_2Ir(acac)$ [bis-(1-phenylisoquinolyl)iridium(III)acetylacetonate] as a dopant in a weight ratio of 95:5. (1,1'-bisphenyl)-4-olato)bis(2-methyl-8-quinolinolato)aluminum (hereinafter will be abbreviated as BAlq) was vacuum deposited to form a hole blocking layer with a thickness of 10 nm, and an electron transport layer was formed using tris(8-quinolinol)aluminum (hereinafter will be abbreviated as Alq3) to a thickness of 40 nm. After that, an alkali metal halide, LiF was deposited as an electron injection layer to a thickness of 0.2 nm, and Al was deposited as a cathode to a thickness of 150 nm to manufacture an OLED.

TABLE 3

| compound | FD-MS | compound | FD-MS |
|---|---|---|---|
| P-1 | m/z = 624.17($C_{42}H_{28}N_2S_2$ = 624.82) | P-2 | m/z = 624.17($C_{42}H_{28}N_2S_2$ = 624.82) |
| P-3 | m/z = 608.19($C_{42}H_{28}N_2OS$ = 608.76) | P-4 | m/z = 608.19($C_{42}H_{28}N_2OS$ = 608.76) |
| P-5 | m/z = 624.17($C_{42}H_{28}N_2S_2$ = 624.82) | P-6 | m/z = 624.17($C_{42}H_{28}N_2S_2$ = 624.82) |
| P-7 | m/z = 608.19($C_{42}H_{28}N_2OS$ = 608.76) | P-8 | m/z = 608.19($C_{42}H_{28}N_2OS$ = 608.76) |
| P-9 | m/z = 700.20($C_{48}H_{32}N_2S_2$ = 700.92) | P-10 | m/z = 700.20($C_{48}H_{32}N_2S_2$ = 700.92) |
| P-11 | m/z = 684.22($C_{48}H_{32}N_2OS$ = 684.86) | P-12 | m/z = 684.22($C_{48}H_{32}N_2OS$ = 684.86) |
| P-13 | m/z = 700.20($C_{48}H_{32}N_2S_2$ = 700.92) | P-14 | m/z = 700.20($C_{48}H_{32}N_2S_2$ = 700.92) |
| P-15 | m/z = 708.22($C_{48}H_{32}N_2OS$ = 708.88) | P-16 | m/z = 658.21($C_{46}H_{30}N_2OS$ = 658.82) |
| P-17 | m/z = 724.20($C_{50}H_{32}N_2S_2$ = 724.94) | P-18 | m/z = 638.19($C_{43}H_{30}N_2S_2$ = 638.85) |
| P-19 | m/z = 714.18($C_{48}H_{30}N_2OS_2$ = 714.90) | P-20 | m/z = 622.21($C_{43}H_{30}N_2OS$ = 622.79) |
| P-21 | m/z = 730.16($C_{48}H_{30}N_2S_3$ = 730.96) | P-22 | m/z = 789.23($C_{54}H_{35}N_3S_2$ = 790.02) |
| P-23 | m/z = 758.24($C_{54}H_{34}N_2OS$ = 758.94) | P-24 | m/z = 724.25($C_{51}H_{36}N_2OS$ = 724.92) |
| P-25 | m/z = 730.16($C_{48}H_{30}N_2S_3$ = 730.96) | P-26 | m/z = 730.16($C_{48}H_{30}N_2S_3$ = 730.96) |
| P-27 | m/z = 698.20($C_{48}H_{30}N_2O_2S$ = 698.84) | P-28 | m/z = 714.18($C_{48}H_{30}N_2OS_2$ = 714.90) |
| P-29 | m/z = 701.20($C_{47}H_{31}N_3S_2$ = 701.91) | P-30 | m/z = 789.23($C_{54}H_{35}N_3S_2$ = 790.02) |
| P-31 | m/z = 760.25($C_{54}H_{36}N_2OS$ = 760.96) | P-32 | m/z = 760.25($C_{54}H_{36}N_2OS$ = 760.96) |
| P-33 | m/z = 700.20($C_{48}H_{32}N_2S_2$ = 700.92) | P-34 | m/z = 839.24($C_{58}H_{37}N_3S_2$ = 840.08) |
| P-35 | m/z = 760.25($C_{54}H_{36}N_2OS$ = 760.96) | P-36 | m/z = 758.24($C_{54}H_{34}N_2OS$ = 758.94) |
| P-37 | m/z = 730.16($C_{48}H_{30}N_2S_3$ = 730.96) | P-38 | m/z = 724.20($C_{50}H_{32}N_2S_2$ = 724.94) |
| P-39 | m/z = 708.22($C_{48}H_{32}N_2OS$ = 708.88) | P-40 | m/z = 636.22($C_{44}H_{32}N_2OS$ = 636.81) |
| P-41 | m/z = 836.14($C_{54}H_{32}N_2S_4$ = 837.10) | P-42 | m/z = 730.16($C_{48}H_{30}N_2S_3$ = 730.96) |
| P-43 | m/z = 698.20($C_{48}H_{30}N_2O_2S$ = 698.84) | P-44 | m/z = 684.22($C_{48}H_{32}N_2OS$ = 684.86) |
| P-45 | m/z = 789.23($C_{54}H_{35}N_3S_2$ = 790.02) | P-46 | m/z = 800.23($C_{56}H_{36}N_2S_2$ = 801.04) |
| P-47 | m/z = 748.25($C_{53}H_{36}N_2OS$ = 748.94) | P-48 | m/z = 899.30($C_{64}H_{41}N_3OS$ = 900.11) |
| P-49 | m/z = 863.26($C_{60}H_{37}N_3O_2S$ = 864.04) | P-50 | m/z = 806.19($C_{54}H_{34}N_2S_3$ = 807.06) |
| P-51 | m/z = 748.22($C_{52}H_{32}N_2O_2S$ = 748.90) | P-52 | m/z = 949.31($C_{68}H_{43}N_3OS$ = 950.17) |
| P-53 | m/z = 674.19($C_{46}H_{30}N_2S_2$ = 674.88) | P-54 | m/z = 674.19($C_{46}H_{30}N_2S_2$ = 674.88) |
| P-55 | m/z = 658.21($C_{46}H_{30}N_2OS$ = 658.82) | P-56 | m/z = 658.21($C_{46}H_{30}N_2OS$ = 658.82) |
| P-57 | m/z = 764.20($C_{52}H_{32}N_2OS_2$ = 764.96) | P-58 | m/z = 886.16($C_{58}H_{34}N_2S_4$ = 887.16) |
| P-59 | m/z = 748.22($C_{52}H_{32}N_2O_2S$ = 748.90) | P-60 | m/z = 810.27($C_{58}H_{38}N_2OS$ = 811.02) |
| P-61 | m/z = 674.19($C_{46}H_{30}N_2S_2$ = 674.88) | P-62 | m/z = 674.19($C_{46}H_{30}N_2S_2$ = 674.88) |
| P-63 | m/z = 658.21($C_{46}H_{30}N_2OS$ = 658.82) | P-64 | m/z = 658.21($C_{46}H_{30}N_2OS$ = 658.82) |
| P-65 | m/z = 780.17($C_{52}H_{32}N_2S_3$ = 781.02) | P-66 | m/z = 750.22($C_{52}H_{34}N_2S_2$ = 750.98) |
| P-67 | m/z = 658.21($C_{46}H_{30}N_2OS$ = 658.82) | P-68 | m/z = 824.25($C_{58}H_{36}N_2O_2S$ = 825.00) |
| P-69 | m/z = 700.20($C_{48}H_{32}N_2S_2$ = 700.92) | P-70 | m/z = 700.20($C_{48}H_{32}N_2S_2$ = 700.92) |
| P-71 | m/z = 684.22($C_{48}H_{32}N_2OS$ = 684.86) | P-72 | m/z = 760.25($C_{54}H_{36}N_2OS$ = 760.96) |
| P-73 | m/z = 700.20($C_{48}H_{32}N_2S_2$ = 700.92) | P-74 | m/z = 750.22($C_{52}H_{34}N_2S_2$ = 750.98) |
| P-75 | m/z = 684.22($C_{48}H_{32}N_2OS$ = 684.86) | P-76 | m/z = 836.29($C_{60}H_{40}N_2OS$ = 837.05) |

To the OLEDs which were manufactured in examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 2500 cd/m². In the following table, the results on the manufacture of a device and evaluation are shown.

COMPARATIVE EXAMPLE 1

Except for not using EBL, an OLED was manufactured in the same manner as described in the embodiment 1 above.

COMPARATIVE EXAMPLE 2 TO COMPARATIVE EXAMPLE 5

Except that the comparative compound A to C was used as the materials of emitting-auxiliary layer, an OLED was manufactured in the same manner as described in the embodiment 1 above.

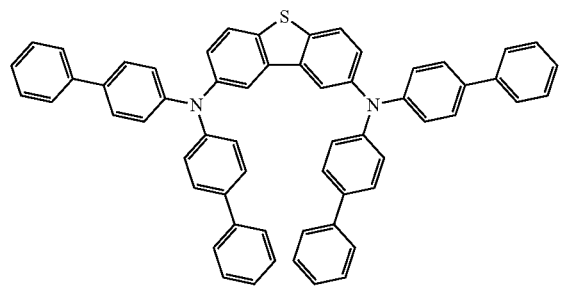

Comparative Compound A

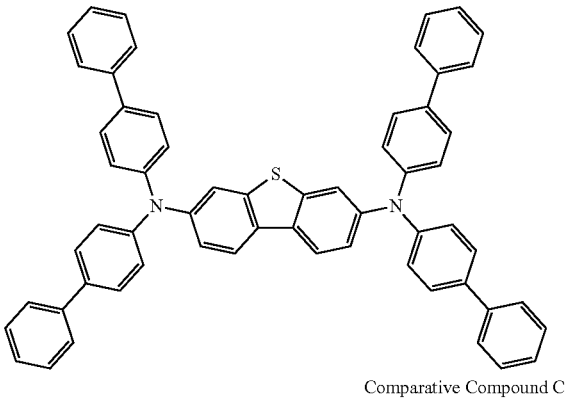

Comparative Compound B

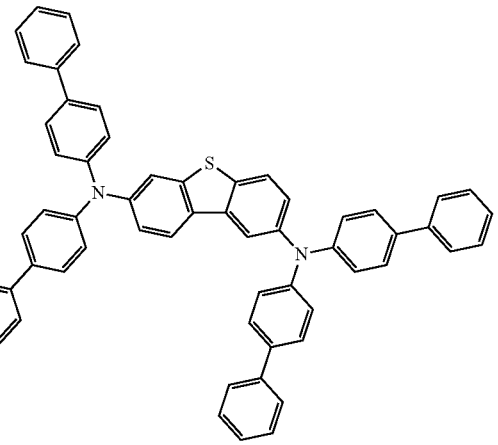

Comparative Compound C

TABLE 4

|  | compound | Voltage | Current Density | Brightness (cd/m2) | Efficiency | Lifetime T (95) | CIE (x, y) |
|---|---|---|---|---|---|---|---|
| Comparative Example (1) | — | 6.0 | 32.9 | 2500.0 | 7.6 | 61.8 | (0.66, 0.32) |
| Comparative Example (2) | comparative compound A | 5.9 | 22.1 | 2500.0 | 11.3 | 88.7 | (0.67, 0.32) |
| Comparative Example (3) | comparative compound B | 5.8 | 23.1 | 2500.0 | 10.8 | 90.1 | (0.66, 0.35) |
| Comparative Example (4) | comparative compound C | 5.6 | 16.4 | 2500.0 | 15.2 | 114.3 | (0.66, 0.35) |
| Example (1) | compound (P-1) | 5.0 | 10.9 | 2500.0 | 23.0 | 114.8 | (0.66, 0.32) |
| Example (2) | compound (P-2) | 5.0 | 10.9 | 2500.0 | 22.8 | 117.6 | (0.66, 0.35) |
| Example (3) | compound (P-3) | 5.0 | 10.2 | 2500.0 | 24.4 | 118.0 | (0.66, 0.35) |
| Example (4) | compound (P-4) | 5.0 | 11.4 | 2500.0 | 22.0 | 117.3 | (0.65, 0.35) |
| Example (5) | compound (P-5) | 5.0 | 11.0 | 2500.0 | 22.8 | 110.2 | (0.65, 0.35) |
| Example (6) | compound (P-6) | 4.9 | 10.2 | 2500.0 | 24.6 | 113.9 | (0.66, 0.35) |
| Example (7) | compound (P-7) | 5.0 | 10.0 | 2500.0 | 24.9 | 118.7 | (0.66, 0.35) |
| Example (8) | compound (P-8) | 5.0 | 10.4 | 2500.0 | 24.0 | 113.2 | (0.66, 0.35) |
| Example (9) | compound (P-9) | 5.1 | 10.9 | 2500.0 | 23.0 | 116.8 | (0.66, 0.35) |
| Example (10) | compound (P-10) | 5.0 | 10.8 | 2500.0 | 23.2 | 110.8 | (0.66, 0.35) |
| Example (11) | compound (P-11) | 5.0 | 10.8 | 2500.0 | 23.2 | 116.6 | (0.66, 0.35) |
| Example (12) | compound (P-12) | 5.0 | 10.6 | 2500.0 | 23.6 | 113.4 | (0.66, 0.35) |
| Example (13) | compound (P-13) | 4.9 | 10.9 | 2500.0 | 23.0 | 115.3 | (0.66, 0.35) |
| Example (14) | compound (P-14) | 4.9 | 11.1 | 2500.0 | 22.5 | 111.1 | (0.66, 0.35) |
| Example (15) | compound (P-15) | 5.1 | 10.9 | 2500.0 | 22.9 | 110.7 | (0.66, 0.35) |
| Example (16) | compound (P-16) | 5.1 | 10.2 | 2500.0 | 24.5 | 118.3 | (0.66, 0.35) |
| Example (17) | compound (P-17) | 4.9 | 11.1 | 2500.0 | 22.6 | 111.7 | (0.66, 0.35) |
| Example (18) | compound (P-18) | 4.9 | 10.7 | 2500.0 | 23.3 | 119.5 | (0.66, 0.35) |
| Example (19) | compound (P-19) | 4.9 | 11.0 | 2500.0 | 22.7 | 112.9 | (0.66, 0.35) |
| Example (20) | compound (P-20) | 5.1 | 10.6 | 2500.0 | 23.7 | 112.3 | (0.66, 0.35) |
| Example (21) | compound (P-21) | 5.0 | 10.5 | 2500.0 | 23.8 | 113.8 | (0.66, 0.35) |
| Example (22) | compound (P-22) | 5.0 | 10.0 | 2500.0 | 24.9 | 112.0 | (0.66, 0.35) |
| Example (23) | compound (P-23) | 4.9 | 10.4 | 2500.0 | 24.1 | 112.8 | (0.66, 0.35) |

TABLE 4-continued

| | compound | Voltage | Current Density | Brightness (cd/m2) | Efficiency | Lifetime T (95) | CIE (x, y) |
|---|---|---|---|---|---|---|---|
| Example (24) | compound (P-24) | 5.0 | 11.1 | 2500.0 | 22.5 | 112.5 | (0.66, 0.35) |
| Example (25) | compound (P-25) | 5.0 | 11.2 | 2500.0 | 22.4 | 119.2 | (0.66, 0.35) |
| Example (26) | compound (P-26) | 5.1 | 10.5 | 2500.0 | 23.8 | 119.4 | (0.66, 0.35) |
| Example (27) | compound (P-27) | 5.0 | 11.1 | 2500.0 | 22.5 | 114.5 | (0.66, 0.35) |
| Example (28) | compound (P-28) | 5.1 | 11.0 | 2500.0 | 22.7 | 119.5 | (0.66, 0.35) |
| Example (29) | compound (P-29) | 4.9 | 10.9 | 2500.0 | 22.8 | 117.9 | (0.66, 0.35) |
| Example (30) | compound (P-30) | 5.0 | 10.4 | 2500.0 | 23.9 | 113.2 | (0.66, 0.35) |
| Example (31) | compound (P-31) | 5.1 | 11.0 | 2500.0 | 22.7 | 114.5 | (0.66, 0.35) |
| Example (32) | compound (P-32) | 5.1 | 10.8 | 2500.0 | 23.2 | 114.7 | (0.66, 0.35) |
| Example (33) | compound (P-33) | 5.0 | 10.2 | 2500.0 | 24.6 | 113.0 | (0.66, 0.35) |
| Example (34) | compound (P-34) | 4.9 | 11.2 | 2500.0 | 22.2 | 116.5 | (0.66, 0.35) |
| Example (35) | compound (P-35) | 5.0 | 10.5 | 2500.0 | 23.7 | 110.0 | (0.66, 0.35) |
| Example (36) | compound (P-36) | 5.0 | 10.2 | 2500.0 | 24.4 | 111.1 | (0.66, 0.35) |
| Example (37) | compound (P-37) | 5.0 | 10.7 | 2500.0 | 23.3 | 115.4 | (0.66, 0.35) |
| Example (38) | compound (P-38) | 5.1 | 11.3 | 2500.0 | 22.1 | 112.2 | (0.66, 0.35) |
| Example (39) | compound (P-39) | 5.0 | 10.8 | 2500.0 | 23.1 | 115.5 | (0.66, 0.35) |
| Example (40) | compound (P-40) | 5.0 | 11.0 | 2500.0 | 22.6 | 118.8 | (0.66, 0.35) |
| Example (41) | compound (P-41) | 4.9 | 11.0 | 2500.0 | 22.8 | 115.8 | (0.66, 0.35) |
| Example (42) | compound (P-42) | 5.1 | 11.1 | 2500.0 | 22.5 | 117.1 | (0.66, 0.35) |
| Example (43) | compound (P-43) | 4.9 | 10.3 | 2500.0 | 24.3 | 110.4 | (0.66, 0.35) |
| Example (44) | compound (P-44) | 4.9 | 10.3 | 2500.0 | 24.2 | 119.8 | (0.66, 0.35) |
| Example (45) | compound (P-45) | 4.9 | 11.0 | 2500.0 | 22.7 | 118.5 | (0.66, 0.35) |
| Example (46) | compound (P-46) | 5.1 | 10.7 | 2500.0 | 23.4 | 114.8 | (0.66, 0.35) |
| Example (47) | compound (P-47) | 5.0 | 10.3 | 2500.0 | 24.4 | 117.4 | (0.66, 0.32) |
| Example (48) | compound (P-48) | 5.0 | 11.3 | 2500.0 | 22.2 | 113.9 | (0.67, 0.32) |
| Example (49) | compound (P-49) | 4.9 | 10.5 | 2500.0 | 23.9 | 113.3 | (0.66, 0.32) |
| Example (50) | compound (P-50) | 5.0 | 10.7 | 2500.0 | 23.4 | 112.7 | (0.66, 0.35) |
| Example (51) | compound (P-51) | 5.0 | 11.1 | 2500.0 | 22.5 | 115.9 | (0.66, 0.35) |
| Example (52) | compound (P-52) | 4.9 | 10.3 | 2500.0 | 24.4 | 114.6 | (0.65, 0.35) |
| Example (53) | compound (P-53) | 5.3 | 13.3 | 2500.0 | 18.7 | 115.6 | (0.65, 0.35) |
| Example (54) | compound (P-54) | 5.3 | 13.3 | 2500.0 | 18.8 | 115.9 | (0.66, 0.32) |
| Example (55) | compound (P-55) | 5.2 | 13.1 | 2500.0 | 19.1 | 115.3 | (0.67, 0.32) |
| Example (56) | compound (P-56) | 5.2 | 13.0 | 2500.0 | 19.2 | 110.0 | (0.66, 0.35) |
| Example (57) | compound (P-57) | 5.2 | 12.0 | 2500.0 | 20.8 | 117.1 | (0.66, 0.35) |
| Example (58) | compound (P-58) | 5.3 | 12.0 | 2500.0 | 20.8 | 111.1 | (0.66, 0.32) |
| Example (59) | compound (P-59) | 5.3 | 12.8 | 2500.0 | 19.6 | 110.5 | (0.66, 0.35) |
| Example (60) | compound (P-60) | 5.1 | 13.4 | 2500.0 | 18.6 | 116.2 | (0.66, 0.35) |
| Example (61) | compound (P-61) | 5.3 | 13.5 | 2500.0 | 18.5 | 110.9 | (0.65, 0.35) |
| Example (62) | compound (P-62) | 5.2 | 12.5 | 2500.0 | 20.0 | 118.9 | (0.65, 0.35) |
| Example (63) | compound (P-63) | 5.3 | 12.8 | 2500.0 | 19.6 | 111.2 | (0.66, 0.35) |
| Example (64) | compound (P-64) | 5.2 | 13.0 | 2500.0 | 19.2 | 113.5 | (0.66, 0.35) |
| Example (65) | compound (P-65) | 5.2 | 12.6 | 2500.0 | 19.8 | 119.8 | (0.66, 0.35) |
| Example (66) | compound (P-66) | 5.2 | 12.8 | 2500.0 | 19.6 | 115.4 | (0.66, 0.35) |
| Example (67) | compound (P-67) | 5.3 | 12.4 | 2500.0 | 20.1 | 114.6 | (0.66, 0.35) |
| Example (68) | compound (P-68) | 5.2 | 12.7 | 2500.0 | 19.8 | 114.9 | (0.66, 0.35) |
| Example (69) | compound (P-69) | 5.2 | 12.3 | 2500.0 | 20.3 | 118.7 | (0.66, 0.35) |
| Example (70) | compound (P-70) | 5.3 | 12.6 | 2500.0 | 19.8 | 118.9 | (0.66, 0.35) |
| Example (71) | compound (P-71) | 5.2 | 13.7 | 2500.0 | 18.2 | 110.0 | (0.66, 0.35) |
| Example (72) | compound (P-72) | 5.3 | 12.7 | 2500.0 | 19.7 | 114.8 | (0.66, 0.35) |
| Example (73) | compound (P-73) | 5.2 | 13.7 | 2500.0 | 18.3 | 116.3 | (0.66, 0.35) |
| Example (74) | compound (P-74) | 5.3 | 13.4 | 2500.0 | 18.7 | 113.9 | (0.66, 0.35) |
| Example (75) | compound (P-75) | 5.2 | 12.4 | 2500.0 | 20.2 | 117.8 | (0.66, 0.35) |
| Example (76) | compound (P-76) | 5.2 | 10.5 | 2500.0 | 23.9 | 119.8 | (0.66, 0.35) |

As it is apparent from the results of Table 4, when a red organic electroluminescent device is manufactured using a compound of the present invention as an emitting auxiliary layer material, the driving voltage of the organic electroluminescence device can be lowered and the luminous efficiency and lifespan can be remarkably improved as compared with the comparative examples not using the luminescent auxiliary layer or using the comparative compounds A to C.

In other words, the results of Comparative Examples 2 to 4 using the comparative compounds A to C were superior to those of Comparative Example 1 in which the emitting auxiliary layer was not used. Examples 1 to 76 of the compounds of the present invention, which are similar to the inventive compounds, but in which specific substituents such as Dibenzothiophen or Dibenzofuran must be substituted, showed the best results.

Comparing the results of the comparative compounds A to C, it can be confirmed that the result of Comparative Compound C substituted with 2 and 3 in the Dibenzothiophen core is most excellent. Even though the cores are the same, the energy level values (especially the HOMO level) varies depending on the substitution position, and as the physical properties of the compound are changed, it plays a major role as a main factor in improving the device performance during the device deposition. Therefore, it can be confirmed that these different results are obtained.

Comparing the results of Comparative Example C with those of Examples 1 to 76, the amino group is substituted asymmetrically at positions 2 and 3 in dibenzothiophen as in comparative compound C, but it can be confirmed that the inventive compound substituted with a specific substituent such as dibenzothiophene or dibenzofuran is remarkably superior in the result. This suggests that even if the substitution position is the same, the kind of the substituent is different and significantly different results may be obtained. When dibenzothiophene or dibenzofuran is introduced to a substituent, the refractive index is remarkably higher than that of the substitution of the substituent of an aryl group, Tg is also increased, such that the efficiency and the thermal stability become excellent, and it was judged that these differences showed remarkably excellent device results as in Examples 1 to 76.

Therefore, in conclusion, it can be confirmed that the compound of the present substituted with the amino group introduced with a specific substituent such as Dibenzothiophen or Dibenzofuran asymmetrically at positions 2 and 3 in the dibenzothiophen core is remarkably superior to the conventional similar compounds.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

| [Explanation of Reference Numerals] | |
|---|---|
| 100: organic electric element | 110: substrate |
| 120: the first electrode (anode) | 130: the hole injection layer |
| 140: the hole transport layer | 141: a buffer layer |
| 150: the emitting layer | 151: the emitting-auxiliary layer |
| 160: the electron transport layer | 170: the electron injection layer |
| 180: the second electrode (cathode) | |

The invention claimed is:

1. A compound represented by Formula (1) below:

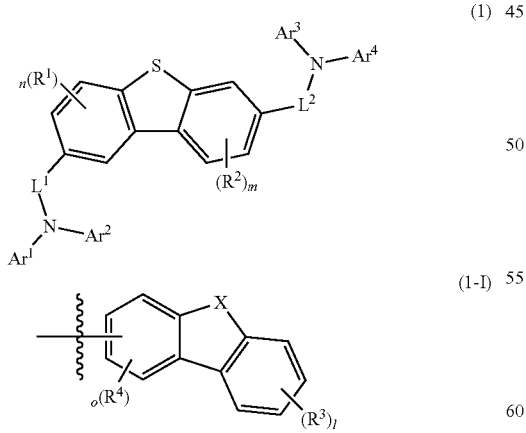

wherein:

1) $Ar^1$, $Ar^2$, $Ar^3$ and $Ar^4$ are each independently selected from the group consisting of: a halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$), or may combine to form an aromatic ring or a hetero-aromatic ring by condensation of adjacent groups to a ring, wherein at least one of $Ar^1$, $Ar^2$, $Ar^3$ and $Ar^4$ is a substituent represented by Formula (1-1) above, 2) $L^1$ and $L^2$ are each selected from the group consisting of: a single bond; a $C_6$-$C_{60}$ arylene group; a fluorenylene group; and a $C_2$-$C_{60}$ hetero arylene group including at least one hetero atom of O, N, S, Si or P, 3) l is an integer of 0 to 4 and m, n and o are each an integer of 0 to 3, wherein at least one of l and o is an integer of 2 or more, 4) $R^1$, $R^2$, $R^3$ and $R^4$ are each independently selected from the group consisting of: hydrogen; deuterium; halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R_a$)($R_b$), wherein when $R^1$ or $R^2$ is plural, a plurality of $R^1$ or a plurality of $R^2$ may combine to each other to form a ring, and wherein $R^3$ and/or $R^4$ are plural, and a plurality of $R^3$ and/or a plurality of $R^4$ combine to each other to form a ring, 5) X is O or S, and 6) In -L'-N($R_a$)($R_b$) above, L' is selected from the group consisting of: a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and $R_a$ and $R_b$ are each independently selected from the group consisting of: a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom selected from the group consisting of O, N, S, Si, and P, wherein, the aryl group; fluorenyl group; arylene group; heterocyclic group; fused ring group described above may be substituted by one or more of the substituent(s) selected from the group consisting of: deuterium; halogen; a silane group; a siloxan group; a boron group; a germanium group; a cyano group; a nitro group; -L'-N($R_a$)($R_b$); a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted by deuterium; fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group and also may combine to each other to form a saturated or unsaturated ring selected from the group consisting of: an aliphatic ring having 3 to 60 carbon atoms, an aromatic ring having 6 to 60 carbon atoms, a hetero ring having 2 to 60 carbon atoms, and a fused ring formed by the combination of them.

2. The compound according to claim 1 represented by Formula (2) or Formula (3) below:

77
Formula (2)
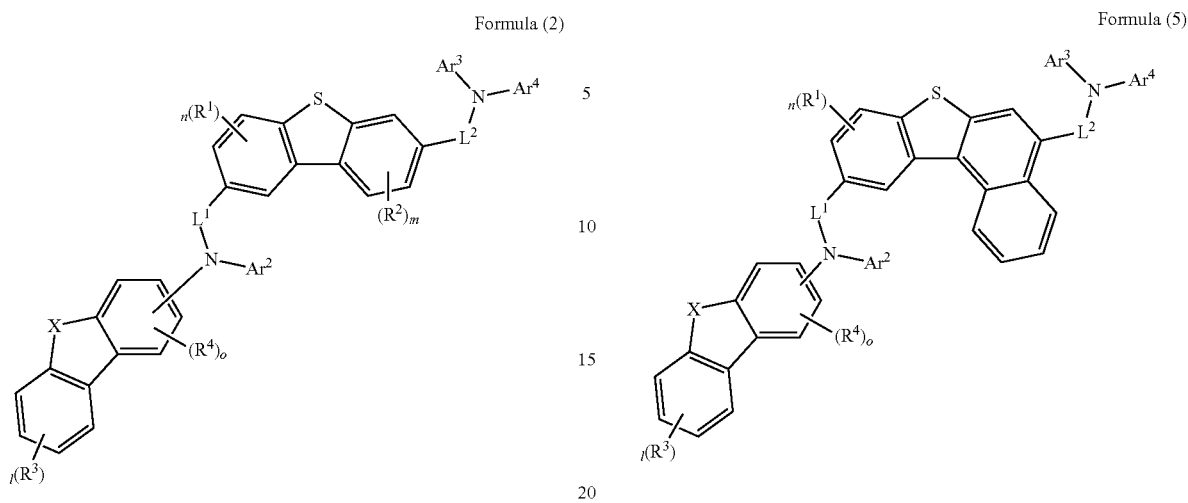
Formula (3)
wherein R¹, R², R³, R⁴, l, m, n, o, Ar¹, Ar², Ar³, Ar⁴, L¹, L², X are the same as defined in claim 1.
3. The compound according to claim 1 represented by any of Formula (4) to Formula (9) below:
Formula (4)
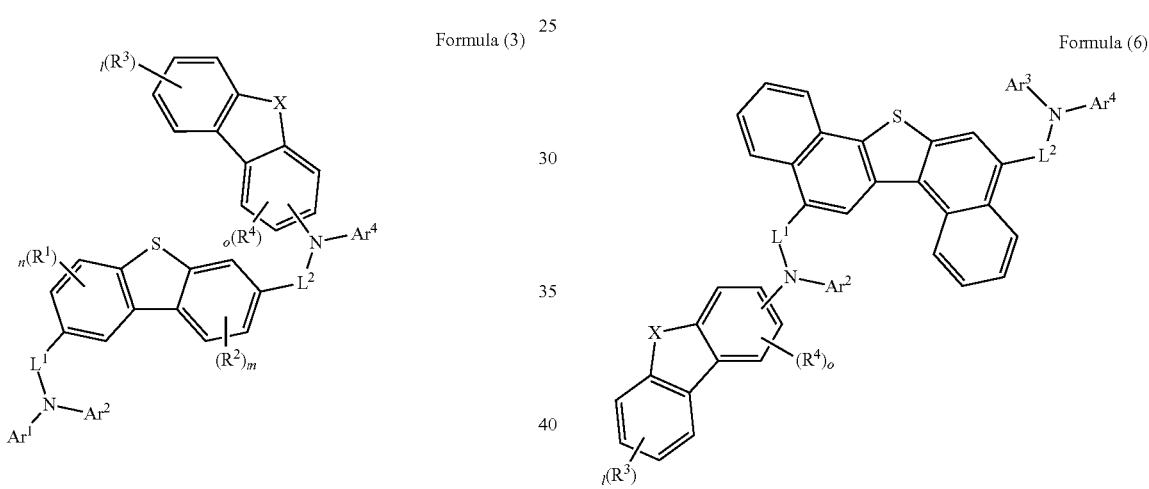
78
-continued
Formula (5)
Formula (6)
Formula (7)
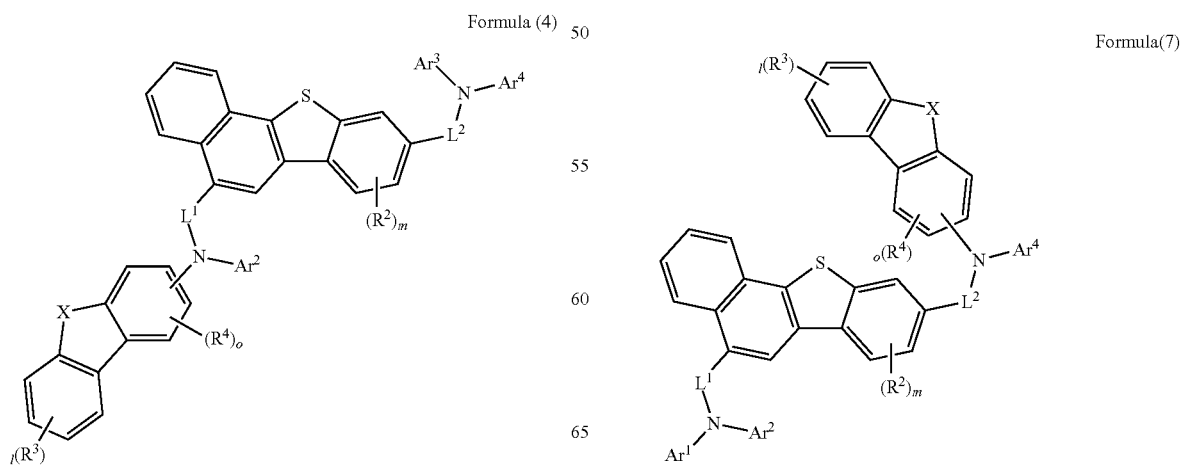

Formula(8)

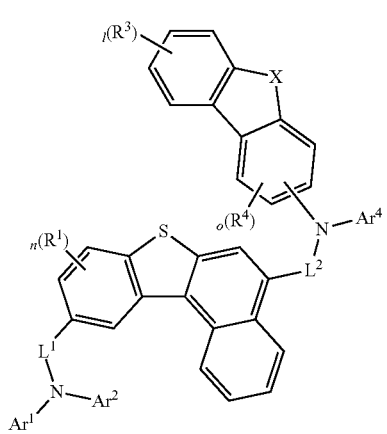

Formula(9)

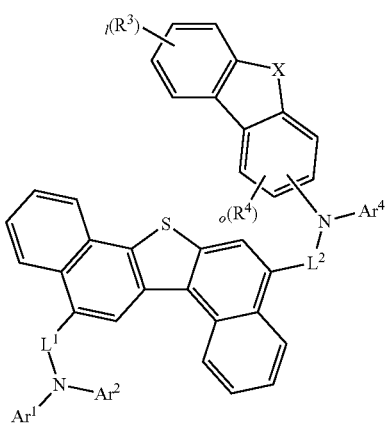

wherein $R^1$, $R^2$, $R^3$, $R^4$, l, m, n, o, $Ar^1$, $Ar^2$, $Ar^3$, $A^4$, $L^1$, $L^2$, X are the same as defined in claim 1.

4. The compound according to claim 1 represented by any of the following compounds:

P-46

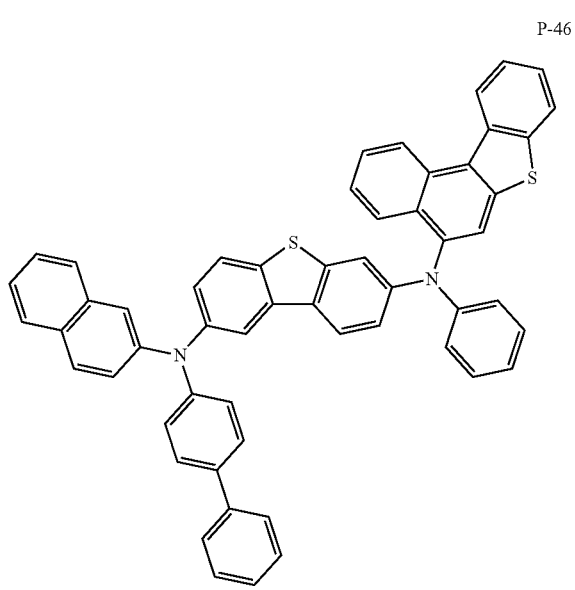

P-51

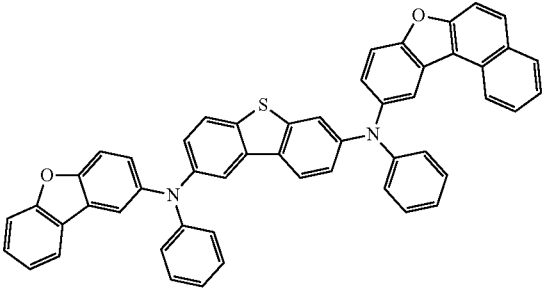

P-52

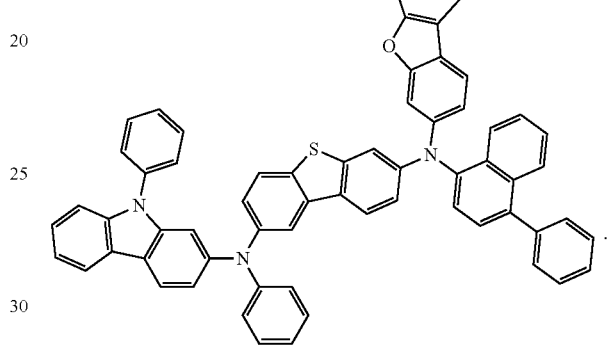

5. An organic electric element comprising: a first electrode; a second electrode; and an organic material layer positioned between the first electrode and the second electrode, wherein the organic material layer comprises one or more of the compounds according to claim 1.

6. The organic electric element according to claim 5, wherein the organic material layer is selected from the group consisting of a hole injection layer, a hole transport layer, an emitting-auxiliary layer, and an emitting layer, and contains one or more of the compounds.

7. The organic electric element according to claim 6, wherein the organic material layer is a hole transport layer or an emitting-auxiliary layer.

8. The organic electric element according to claim 5, further comprising a light efficiency enhancing layer formed on one side of the first electrode and/or on one side of the second electrode, the side being opposite to the organic material layer.

9. The organic electric element according to claim 5, wherein the organic material layer is formed by one of a spin coating process, a nozzle printing process, an inkjet printing process, a slot coating process, a dip coating process, and a roll-to-roll process.

10. An electronic device comprising a display apparatus comprising the organic electric element according to claim 5; and a driving part configured to drive the display apparatus.

11. The electronic device according to claim 10, wherein the organic electric element is at least one of an organic light emitting diode (OLED), an organic solar cell, an organic photo conductor, an organic transistor, and a device for monochromic or white illumination.

* * * * *